(12) United States Patent
Sarkar et al.

(10) Patent No.: US 11,806,154 B2
(45) Date of Patent: Nov. 7, 2023

(54) METHOD AND APPARATUS FOR VERIFYING BRADYCARDIA/ASYSTOLE EPISODES VIA DETECTION OF UNDER-SENSED EVENTS

(71) Applicant: Medtronic, Inc., Minneapolis, MN (US)

(72) Inventors: Shantanu Sarkar, Roseville, MN (US); Michael L Hudziak, Stillwater, MN (US); Jerry D. Reiland, Coon Rapids, MN (US); Erin N. Reisfeld, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 58 days.

(21) Appl. No.: 17/454,923

(22) Filed: Nov. 15, 2021

(65) Prior Publication Data

US 2022/0071545 A1 Mar. 10, 2022

Related U.S. Application Data

(60) Continuation of application No. 17/323,836, filed on May 18, 2021, now Pat. No. 11,172,863, which is a (Continued)

(51) Int. Cl.
*A61B 5/363* (2021.01)
*A61B 5/00* (2006.01)
(Continued)

(52) U.S. Cl.
CPC ............. *A61B 5/363* (2021.01); *A61B 5/287* (2021.01); *A61B 5/316* (2021.01); *A61B 5/335* (2021.01);
(Continued)

(58) Field of Classification Search
CPC ......... A61B 5/363; A61B 5/335; A61B 5/352; A61B 5/287; A61B 5/316; A61B 5/6861;
(Continued)

(56) References Cited

U.S. PATENT DOCUMENTS

| 4,374,382 A | 2/1983 | Markowitz |
| 5,117,824 A | 6/1992 | Keimel et al. |

(Continued)

FOREIGN PATENT DOCUMENTS

| EP | 2767222 A1 | 8/2014 |
| WO | 2000047277 A1 | 8/2000 |
| WO | 2010146481 A1 | 12/2010 |

OTHER PUBLICATIONS

Notification of Transmittal of the International Search Report and Written Opinion of the International Searching Authority, or the Declaration for PCT/US2017/021102, dated May 17, 2017.

(Continued)

*Primary Examiner* — Erin M Piateski
(74) *Attorney, Agent, or Firm* — Shumaker & Sieffert, P.A.

(57) ABSTRACT

A system and method for detecting and verifying bradycardia/asystole episodes includes sensing an electrogram (EGM) signal. The EGM signal is compared to a primary threshold to sense events in the EGM signal, and at least one of a bradycardia or an asystole is detected based on the comparison. In response to detecting at least one of a bradycardia or an asystole, the EGM signal is compared to a secondary threshold to sense events under-sensed by the primary threshold. The validity of the bradycardia or the asystole is determined based on the detected under-sensed events.

29 Claims, 13 Drawing Sheets

Related U.S. Application Data continuation of application No. 16/523,297, filed on Jul. 26, 2019, now Pat. No. 11,259,736, which is a division of application No. 15/081,216, filed on Mar. 25, 2016, now Pat. No. 10,413,207.

(51) Int. Cl.

| | | |
|---|---|---|
| *A61B 5/287* | (2021.01) | |
| *A61B 5/316* | (2021.01) | |
| *A61B 5/335* | (2021.01) | |
| *A61B 5/332* | (2021.01) | |
| *A61N 1/365* | (2006.01) | |
| *A61N 1/39* | (2006.01) | |
| *A61B 5/352* | (2021.01) | |
| *A61B 5/364* | (2021.01) | |

(52) U.S. Cl.
CPC .......... *A61B 5/352* (2021.01); *A61B 5/6861* (2013.01); *A61B 5/7221* (2013.01); *A61N 1/36514* (2013.01); *A61N 1/3956* (2013.01); *A61N 1/3987* (2013.01); *A61B 5/364* (2021.01); *A61B 2505/07* (2013.01); *A61B 2560/0468* (2013.01)

(58) Field of Classification Search
CPC ... A61B 5/7221; A61B 5/364; A61B 2505/07; A61B 2560/0468; A61N 1/36514; A61N 1/3956; A61N 1/3987
USPC .......................................................... 600/15
See application file for complete search history.

(56) References Cited

U.S. PATENT DOCUMENTS

| | | | |
|---|---|---|---|
| 5,193,535 | A | 3/1993 | Bardy et al. |
| 5,545,186 | A | 8/1996 | Olson et al. |
| 5,957,857 | A | 9/1999 | Hartley |
| 6,067,473 | A | 5/2000 | Greeninger et al. |
| 6,112,119 | A | 8/2000 | Schuelke et al. |
| 6,236,882 | B1 | 5/2001 | Lee et al. |
| 6,539,259 | B1 | 3/2003 | Weinberg et al. |
| 7,027,858 | B2 | 4/2006 | Cao et al. |
| 7,031,765 | B2 | 4/2006 | Ritcher et al. |
| 7,537,569 | B2 | 5/2009 | Sarkar et al. |
| 7,623,911 | B2 | 11/2009 | Sarkar et al. |
| 7,627,368 | B2 | 12/2009 | Houben et al. |
| 7,899,520 | B2 | 3/2011 | Lian et al. |
| 8,055,342 | B2 | 11/2011 | Zhang et al. |
| 8,639,316 | B2 | 1/2014 | Sarkar |
| 8,774,908 | B2 | 7/2014 | Stewart |
| 8,831,713 | B2 | 9/2014 | Stadler et al. |
| 8,977,350 | B2 | 3/2015 | Sarkar et al. |
| 9,002,470 | B2 | 4/2015 | Reinke et al. |
| 9,486,155 | B2 | 11/2016 | Sarkar et al. |
| 10,413,207 | B2 | 9/2019 | Sarkar et al. |
| 2004/0049120 | A1 | 3/2004 | Cao et al. |
| 2004/0049212 | A1 | 3/2004 | Cao |
| 2006/0241702 | A1 | 10/2006 | Gillberg |
| 2009/0192381 | A1* | 7/2009 | Brockway ............... A61B 5/283 |
| | | | 600/373 |
| 2010/0030293 | A1 | 2/2010 | Sarkar et al. |
| 2010/0094252 | A1 | 4/2010 | Wengreen et al. |
| 2012/0029373 | A1* | 2/2012 | Stadler .................... A61N 1/37 |
| | | | 600/515 |
| 2012/0265085 | A1 | 10/2012 | Doerr et al. |
| 2012/0283705 | A1 | 11/2012 | Lee et al. |
| 2013/0138005 | A1 | 5/2013 | Dong et al. |
| 2014/0236032 | A1 | 8/2014 | Garner |
| 2014/0276154 | A1* | 9/2014 | Katra .................... A61B 5/316 |
| | | | 600/509 |
| 2014/0276928 | A1 | 9/2014 | Vanderpool et al. |
| 2015/0073295 | A1 | 3/2015 | Gordon et al. |
| 2015/0073507 | A1* | 3/2015 | Reinke .................. A61N 1/378 |
| | | | 607/61 |
| 2016/0213273 | A1 | 7/2016 | Cao et al. |
| 2016/0213274 | A1 | 7/2016 | Cao et al. |
| 2016/0213275 | A1 | 7/2016 | Cao et al. |
| 2016/0213941 | A1 | 7/2016 | Zhang et al. |
| 2016/0235317 | A1 | 8/2016 | Sarkar et al. |
| 2016/0235318 | A1 | 8/2016 | Sarkar et al. |
| 2016/0235320 | A1 | 8/2016 | Sarkar et al. |
| 2016/0235321 | A1 | 8/2016 | Sarkar et al. |
| 2016/0235992 | A1 | 8/2016 | Sarkar et al. |
| 2019/0350481 | A1 | 11/2019 | Sarkar et al. |
| 2021/0267528 | A1 | 9/2021 | Sarkar et al. |

OTHER PUBLICATIONS

International Preliminary Report on Patentability from International Application No. PCT/US2017/021102, dated Sep. 25, 2018, 8 pp.
Communication Pursuant to Rules 161(1) and 162 EPC dated Nov. 13, 2018 from counterpart European Application No. 17712600.0-1115, 3 pp.
Response to Communication Pursuant to Rules 161(1) and 162 EPC dated Nov. 13, 2018 from counterpart European Application No. 17712600.0-1115, filed May 23, 2019, 7 pp.
Second Office Action, and translation thereof, from counterpart Chinese Application No. 201780019979.9, dated Jun. 18, 2021, 9 pp.
Prosecution History from U.S. Appl. No. 15/081,216, dated Aug. 15, 2017 through May 20, 2019, 115 pp.
Prosecution History from U.S. Appl. No. 16/523,297, dated Feb. 11, 2021 through Oct. 22, 2021, 32 pp.
Prosecution History from U.S. Appl. No. 17/323,836, dated Jul. 28, 2021 through Oct. 5, 2021, 32 pp.
Notice on Grant of Patent Right for Invention and Notice on Proceeding with the Registration Formalities, and translation thereof, from counterpart Chinese Application No. 2017800199799 dated Dec. 1, 2021, 3 pp.

* cited by examiner

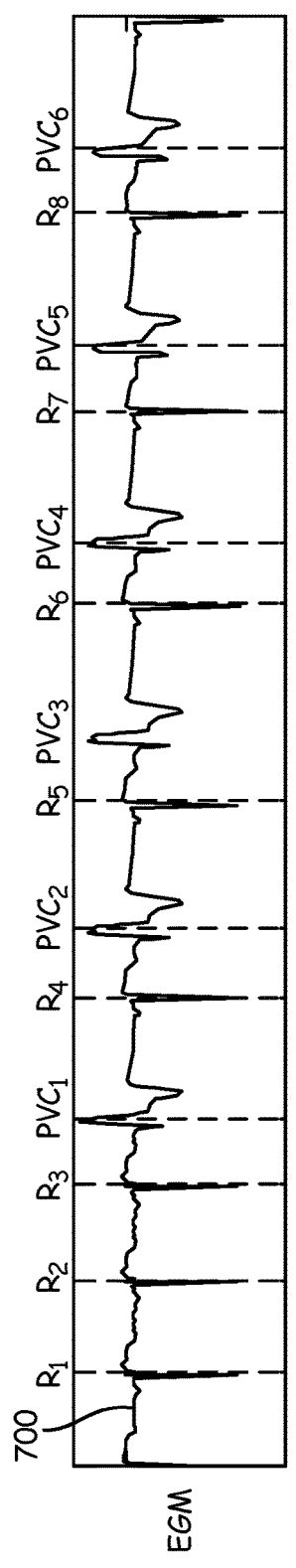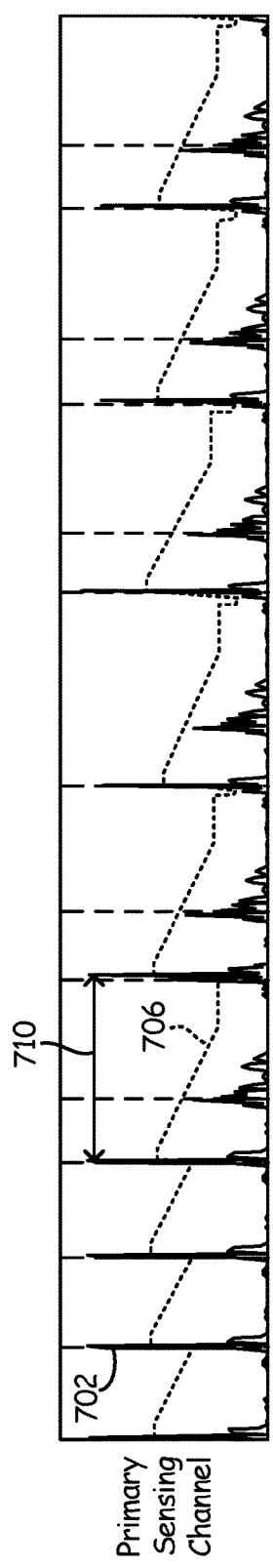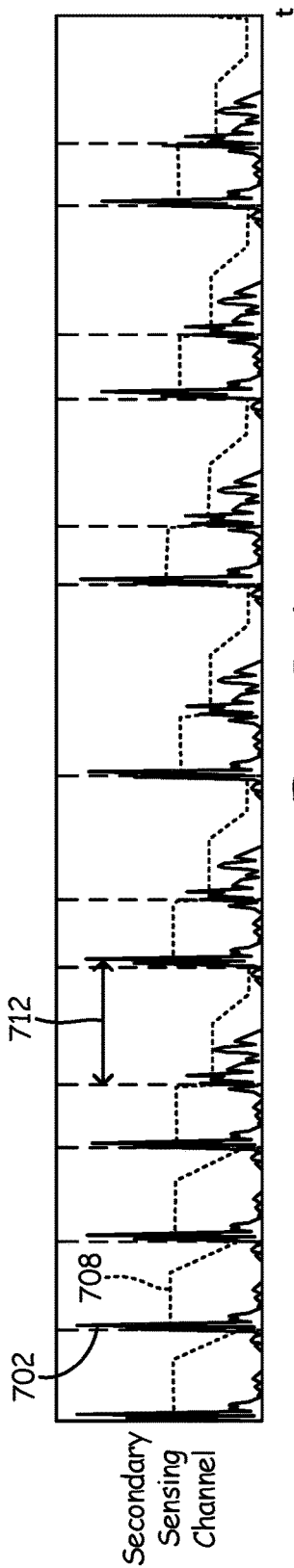

METHOD AND APPARATUS FOR VERIFYING BRADYCARDIA/ASYSTOLE EPISODES VIA DETECTION OF UNDER-SENSED EVENTS

This application is a continuation of U.S. patent application Ser. No. 17/323,836, filed May 18, 2021, which is a continuation of U.S. patent application Ser. No. 16/523,297, filed Jul. 26, 2019, which is a divisional of U.S. patent application Ser. No. 15/081,216, filed Mar. 25, 2016 (now U.S. Pat. No. 10,413,207), the entire contents of each of which is incorporated herein by reference.

TECHNICAL FIELD

The present disclosure is related to medical devices, and in particular to medical devices that sense a signal indicative of cardiac activity.

BACKGROUND

A variety of medical devices exist for monitoring patient cardiac activity. For example, these devices may be implantable, subcutaneous, or adherent and may include one or more leads for monitoring electrical signals, e.g., intrinsic depolarizations of the hearts. Methods are used to extrapolate from the monitored electrical signals various cardiac events such as P-waves, R-waves and T-waves (referred to generically as sensed events). Based on these sensed events, cardiac episodes/conditions can be detected. For example, both bradycardia and asystole episodes are characterized by long pauses between sensed events (e.g., R-waves that signal a ventricular depolarization/contraction). However, a determination that a patient is experiencing a bradycardia or asystole episode is based on the assumption that all events have been properly sensed by the medical device. If the medical device under-senses one or more events within the episode, the medical device may incorrectly determine that the patient is experiencing a bradycardia/asystole type event.

In particular, the primary cause for inappropriate bradycardia/asystole detection is due to frequent premature ventricular contractions (PVCs) characterized by a wide QRS complex, PVCs characterized by a very large QRS amplitude, and small/wide QRS complexes. In the case of PVCs characterized by a wide QRS complex, the low-frequency characteristic of the QRS complex results in the PVC being under-sensed. In the case of PVCs characterized by a very large QRS amplitude, the amplitude of the PVC beat results in the under-sensing of normal QRS amplitudes that following the PVC beat. In both cases, the result of under-sensing events results in an inappropriate detection of a bradycardia/asystole event.

It would therefore be desirable to minimize the inappropriate detection of bradycardia/asystole episodes.

BRIEF SUMMARY OF THE INVENTION

According to an exemplary embodiment, a method includes sensing an electrogram (EGM) signal and comparing an amplitude of the EGM signal to a primary threshold to sense events in the EGM signal. The presence of at least one of a bradycardia or an asystole is detected based on the sensed events, and in response to detecting at least one of a bradycardia or an asystole, the EGM signal is compared to a secondary threshold to sense events under-sensed by the primary threshold. Based on the detection of under-sensed events, a determination is made whether the bradycardia or the asystole is false.

According to an exemplary embodiment, a medical device comprises a sensing unit, a primary sensing channel, a secondary sensing channel and processor. The sensing unit monitors an electrogram (EGM) signal and the primary sensing channel applies a primary threshold to the EGM signal to detect sense events within the EGM signal. The secondary sensing channel applies a secondary threshold to the EGM signal to detect under-sensed events within the EGM signal. The processor detects at least one of bradycardia or asystole based on sense events detected by the primary sensing channel, wherein the processor determines whether the detected bradycardia or asystole is false based on detection of under-sensed events by the secondary sensing threshold.

According to another exemplary embodiment, a medical device comprises a sensing unit, a primary sensing channel, a processor, and a memory unit. The sensing unit monitors an electrogram (EGM) signal and the primary sensing channel applies a primary threshold to the EGM signal to detect sense events within the EGM signal. The processor detects at least one of bradycardia or asystole based on sense events detected by the primary sensing channel. The memory unit stores EGM segments associated with a detected bradycardia or asystole, wherein the processor determines whether the detected bradycardia or asystole is false by applying a secondary threshold to the stored EGM segments to detect under-sensed events in the EGM segments.

According to another exemplary embodiment, a medical device comprises a means for sensing an electrogram (EGM) signal. The medical device further comprises means for comparing an amplitude of the EGM signal to a primary threshold to sense events in the EGM signal and means for detecting at least one of a bradycardia or an asystole based on the sensed events. The medical device further includes means for comparing the EGM signal to a secondary threshold to sense events under-sensed by the primary threshold in response to detecting at least one of a bradycardia or an asystole. The medical device further includes means for determining whether the detection of the bradycardia or the asystole is false based on the detection of under-sensed events.

According to another exemplary embodiment, an insertable cardiac monitor includes a first electrode, second electrode, sensing unit, a primary sensing channel, a secondary sensing channel, and a processor. The first electrode is located at a distal end of the insertable cardiac monitor and the second electrode located at a proximal end of the insertable cardiac monitor. The sensing unit is coupled to the first and second electrode to monitor an electrogram (EGM) signal. The primary sensing channel applies a primary threshold to the EGM signal to detect sense events within the EGM signal, and the processor detects at least one of bradycardia or asystole based on sense events detecting by the primary sensing channel. The secondary sensing channel applies a secondary threshold to the EGM signal to detect under-sensed events within the EGM signal, and the processor determines whether the detected bradycardia or asystole is false based on detection of under-sensed events by the secondary sensing threshold.

BRIEF DESCRIPTION OF THE DRAWINGS

FIG. 7A illustrates an example EGM signal that includes PVC beats; FIG. 7B illustrates analysis of the example EGM signal in a first channel and resulting under-sensing of the PVC beats; and FIG. 7C illustrates analysis of the example EGM signal in a second channel to detect the under-sensed PVC beats.

10A illustrates an example EGM signal that includes a PVC beat.

DETAILED DESCRIPTION

Figure 1:
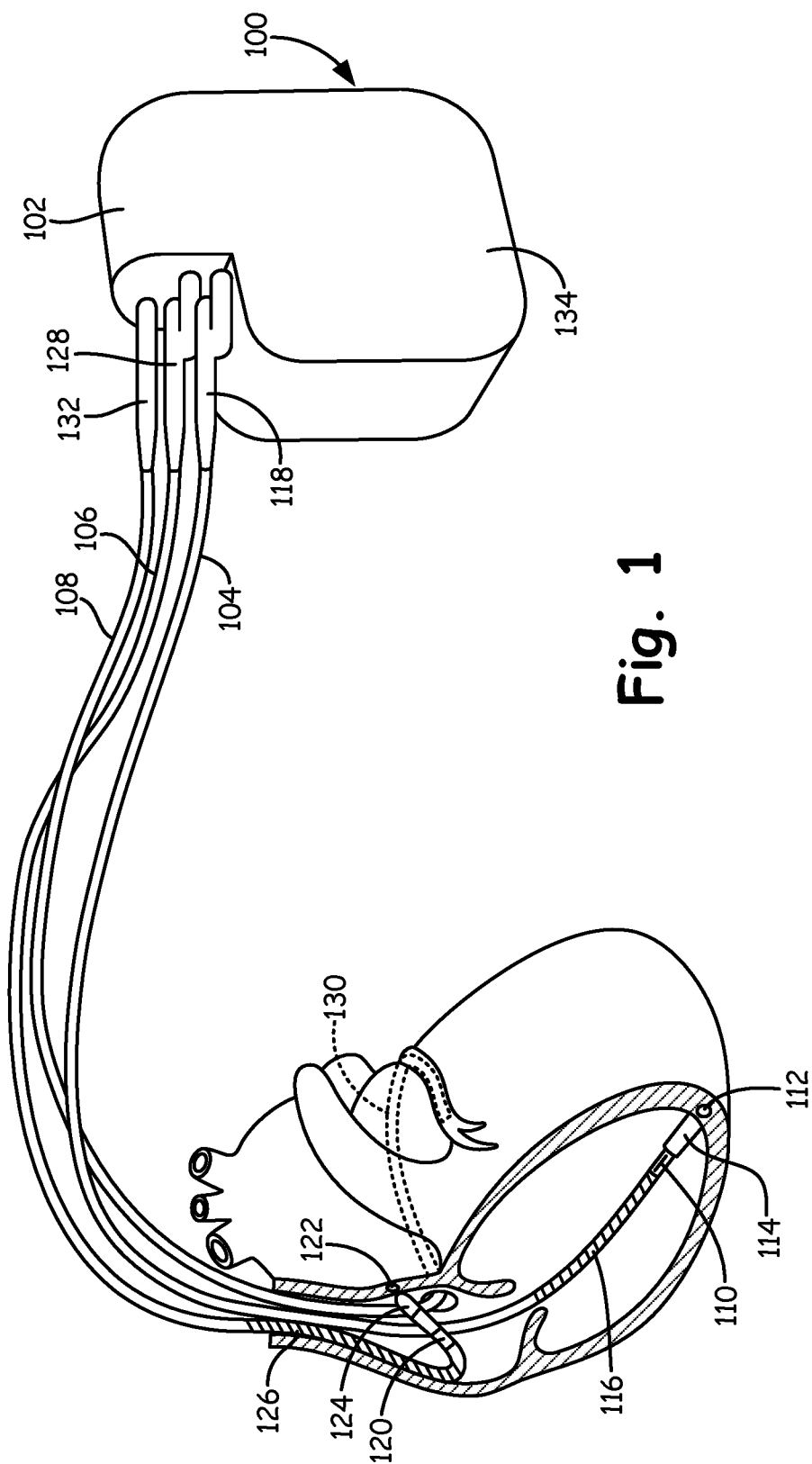
FIG. 1 is a schematic diagram of an exemplary medical device for detecting a bradycardia/asystole event according to an embodiment of the present disclosure.

A variety of medical devices monitor electrogram (EGM) signals of a patient to detect cardiac depolarizations. Based on the monitored EGM signals, the device detects various types of arrhythmias such as fibrillation, tachycardia, bradycardia, and asystole. The term EGM is used herein to refer to any signal received by the medical device via electrodes that indicates electrical activity, e.g., depolarizations and repolarization, of a heart, and may also be referred to as electrocardiogram (ECG) signals. Furthermore, the term "sensed event" is utilized herein to refer to a detected depolarization/repolarization, which may include P-waves, R-waves (included as part of a QRS complex), and T-waves. In general, sensed events refer to detected R-waves utilized to calculate R-R intervals for bradycardia/asystole detection.

Failure of the monitoring device to detect a sensed event (e.g., R-wave) may cause the monitoring device to inappropriately detect a bradycardia or asystole. This failure to detect a sensed event is referred to as under-sensing and may be a result of a variety of factors. For example, in one embodiment the threshold utilized to detect sense events is an auto-adjusting threshold that varies based on the amplitude of a previously sensed event. For example, the auto-adjust threshold may be set to a relatively high value following a detected sense event having a large amplitude, such that subsequent, lower amplitude sense events may be under-sensed. This situation could arise in response to a premature ventricular contraction (PVC) having a very large QRS amplitude, followed by an R-wave characterized by normal QRS amplitudes. In another example, PVCs characterized by a wide QRS complex result in the PVC beats being under-sensed as a result of the low frequency content associated with the wide QRS complex. In yet another example, small and wide QRS complexes may result in under-sensing.

Depending on the type of medical device, in some cases the device provides information regarding detection of arrhythmias, e.g., asystole and bradycardia, for analysis by a clinician. The clinician may make diagnoses of conditions of a patient and, in some cases, prescribe therapy based on the information. A falsely-detected asystole or bradycardia may result in unnecessary delivery of stimulation to a patient by a medical device (e.g., cardiac pacing by a pacemaker). In some cases, a falsely-detected asystole or bradycardia by a medical device may result in inaccurate diagnosis of a patient condition by a clinician who reviews data regarding detection of asystole or bradycardia by the medical device, which in turn may result in unnecessary prescription of a therapy, e.g., pharmaceutical or a device to provide pacing.

In general, this disclosure is directed to signal processing-based technique to prevent the inappropriate detection of bradycardia or asystole without compromising the detection of other arrhythmias (including properly identified bradycardia or asystole). In particular, the disclosure utilizes a first/primary channel to sense events (e.g., R-waves). Based on events sensed in the primary channel, arrhythmic episodes are detected including for example bradycardia and asystole episodes. In response to detection of at least one of a bradycardia or asystole episode, a secondary threshold is utilized to detect sense events under-sensed by the first channel. A bradycardia or asystole episode detected in the first channel is verified based on events detected in the second channel or using a secondary threshold. As described in more detail below, the signal-processing may be implemented in hardware, firmware, or a combination thereof. For example, an exemplary embodiment implemented in hardware may utilize a first channel characterized by a first auto-correct threshold to sense events, and a second channel characterized by a second auto-correct threshold to sense events under-sensed by the first channel. The events (e.g., R-waves) sensed by the first and second channels are combined to determine whether a bradycardia or asystole detected in the first channel was appropriate. In an exemplary embodiment implemented in firmware, an EGM sample in which a bradycardia or asystole episode is detected is stored to memory and analyzed using a secondary threshold to detect under-sensed events. A determination is then made whether the bradycardia or asystole is appropriate based on the events detected using the secondary threshold. In this way, the present disclosure provides a signal-processing system and method for preventing inappropriate detection of bradycardia and/or asystole.

In the following description, references are made to illustrative embodiments for carrying out the methods described herein. It is understood that other embodiments may be utilized without departing from the scope of the disclosure. The methods presented herein may be embodied in software, hardware, firmware or combinations thereof in implantable or external medical devices. Such devices include implantable monitoring devices having cardiac electrogram (EGM)/electrocardiogram (ECG) monitoring capabilities and associated EGM/ECG sense electrodes, which may be intracardiac, epicardial, or subcutaneous electrodes. The methods described herein can also be incorporated in implantable medical devices having therapy delivery capabilities, such as single chamber or bi ventricular pacing systems or ICDs that sense the R-waves in the ventricles and deliver an electrical stimulation therapy to the ventricles. The bradycardia/asystole detection and verification methods presently disclosed may also be incorporated in external monitors having ECG electrodes coupled to the patient's skin to detect R-waves, e.g. Holter monitors, or within computerized systems that analyze prerecorded ECG or EGM data. Embodiments may further be implemented in a patient monitoring system, such as a centralized computer system which processes data sent to it by implantable or wearable monitoring devices, including subcutaneous devices having loop recorders.

FIG. 1 is a schematic diagram of an exemplary medical device for detecting an arrhythmia according to an embodiment of the present disclosure. As illustrated in FIG. 1, an implantable medical device 100 according to an embodiment of the present disclosure may be in the form of an implantable cardioverter defibrillator (ICD) 100 that includes connector block 102 that receives the proximal ends of a right ventricular lead 104, a right atrial lead 106 and a coronary sinus lead 108, used for positioning electrodes for sensing and stimulation in three or four heart chambers. Right ventricular lead 104 is positioned such that its distal end is in the right ventricle for sensing right ventricular cardiac signals and delivering pacing or shocking pulses in the right ventricle. For these purposes, right ventricular lead 104 is equipped with a ring electrode 110, an extendable helix electrode 112 mounted retractably within an electrode head 114, and a coil electrode 116, each of which are connected to an insulated conductor within the body of lead 104. The proximal end of the insulated conductors are coupled to corresponding connectors carried by bifurcated connector 118 at the proximal end of lead 104 for providing electrical connection to the ICD 100. It is understood that although the device illustrated in FIG. 1 is a dual chamber device, other devices such as single chamber devices may be utilized to perform the technique of the present disclosure described herein.

The right atrial lead 106 is positioned such that its distal end is in the vicinity of the right atrium and the superior vena cava. Lead 106 is equipped with a ring electrode 120 and an extendable helix electrode 122, mounted retractably within electrode head 124, for sensing and pacing in the right atrium. Lead 106 is further equipped with a coil electrode 126 for delivering high-energy shock therapy. The ring electrode 120, the helix electrode 122 and the coil electrode 126 are each connected to an insulated conductor with the body of the right atrial lead 106. Each insulated conductor is coupled at its proximal end to a connector carried by bifurcated connector 128.

The coronary sinus lead 108 is advanced within the vasculature of the left side of the heart via the coronary sinus and great cardiac vein. The coronary sinus lead 108 is shown in the embodiment of FIG. 1 as having a defibrillation coil electrode 130 that may be used in combination with either the coil electrode 116 or the coil electrode 126 for delivering electrical shocks for cardioversion and defibrillation therapies. In other embodiments, coronary sinus lead 108 may also be equipped with a distal tip electrode and ring electrode for pacing and sensing functions in the left chambers of the heart. The coil electrode 130 is coupled to an insulated conductor within the body of lead 108, which provides connection to the proximal connector 132.

The electrodes 122 and 120 or 110 and 112 may be used as true bipolar pairs, commonly referred to as a "tip-to-ring" configuration. Further, electrode 122 and coil electrode 116 or electrode 110 and coil electrode 126 may be used as integrated bipolar pairs, commonly referred to as a "tip-to-coil" configuration. In accordance with the invention, ICD 100 may, for example, adjust the electrode configuration from a tip-to ring configuration, e.g., true bipolar sensing, to a tip-to-coil configuration, e.g., integrated bipolar sensing, upon detection of oversensing in order to reduce the likelihood of future oversensing. In other words, the electrode polarities can be reselected in response to detection of oversensing in an effort to reduce susceptibility of oversensing. In some cases, electrodes 122, 120, 110, and 112 may be used individually in a unipolar configuration with the device housing 134 serving as the indifferent electrode, commonly referred to as the "can" or "case" electrode.

The device housing 134 may also serve as a subcutaneous defibrillation electrode in combination with one or more of the defibrillation coil electrodes 130, 116 or 126 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may adapted for use with any single chamber, dual chamber, or multi-chamber ICD or pacemaker system, subcutaneous implantable device, or other internal or external cardiac monitoring device.

ICD 100 may alternatively be configured as a subcutaneous device having sensing or pacing electrodes incorporated on the housing 134 of the device in which case transvenous leads are not required. A subcutaneous device may be coupled to a lead tunneled subcutaneously or submuscularly for delivering transthoracic pacing pulses and/or sensing ECG signals. An exemplary subcutaneous device is described in commonly assigned U.S. patent application Ser. Nos. 14/604,111 and 14/604,260, both incorporated herein by reference in their entireties. The techniques described herein can also be implemented in an external device, e.g. including patch electrodes and optionally another physiological sensor if desired, that can sense variable parameters as described herein.

Figure 2:
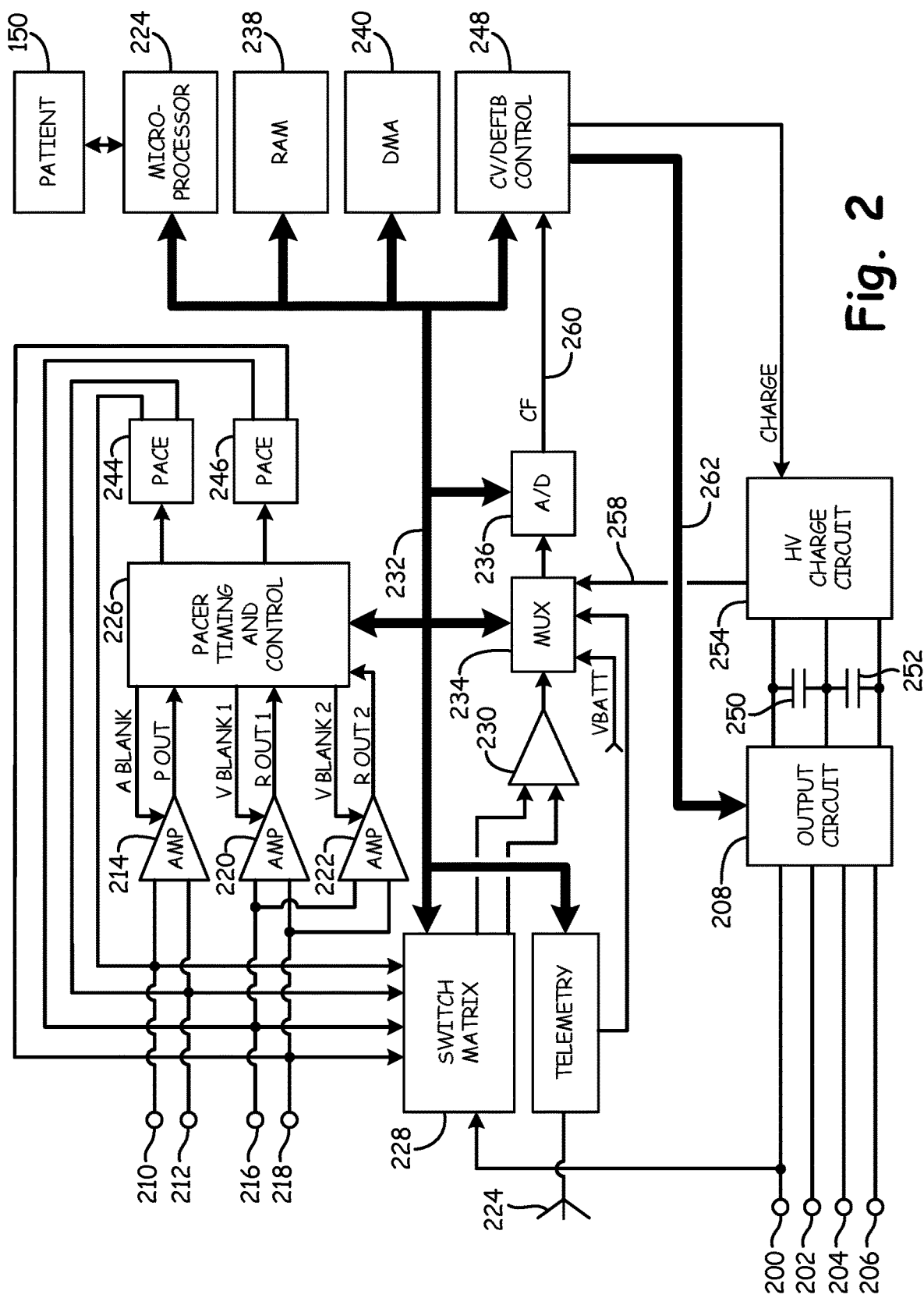
FIG. 2 is a functional schematic diagram of the medical device of FIG. 1 according to an embodiment of the present disclosure.

FIG. 2 is a functional schematic diagram of the medical device of FIG. 1. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, ICD 100 is provided with a number of connection terminals for achieving electrical connection to the leads 104, 106, and 108 and their respective electrodes. A connection terminal 200 provides electrical connection to the housing 134 for use as the indifferent electrode during unipolar stimulation or sensing. The connection terminals 202, 204, and 206 provide electrical connection to coil electrodes 116, 130 and 126 respectively. Each of these connection terminals 200, 202, 204, and 206 are coupled to the high voltage output circuit 208 to facilitate the delivery of high energy shocking pulses to the heart using one or more of the coil electrodes 116, 126, and 130 and optionally the housing 134.

The connection terminals 210 and 212 provide electrical connection to the helix electrode 122 and the ring electrode 120 positioned in the right atrium. The connection terminals 210 and 212 are further coupled to an atrial sense amplifier 214 for sensing atrial signals such as P-waves. The connection terminals 216 and 218 provide electrical connection to the helix electrode 112 and the ring electrode 110 positioned in the right ventricle. The connection terminals 216 and 219 are further coupled to a first ventricular sense amplifier 220 for sensing ventricular signals (i.e., a first ventricular sensing channel). In one embodiment, first ventricular sense amplifier 220 is characterized by a first auto-adjust threshold utilized to sense ventricular events, in particular R-waves (illustrated by the output $R_{OUT1}$) In one embodiment, a second ventricular sense amplifier 222 is also connected to connection terminals 216 and 219 for sensing ventricular events. In one embodiment, second amplifier 222 is characterized by a second auto-adjust threshold utilized to detect ventricular events (e.g., R-waves) under-sensed by the first ventricular sense amplifier 222 (illustrated by the output $R_{OUT2}$). Described in more detail below, this requires the second ventricular sense amplifier 222 to implement a different sensing threshold than the first ventricular sense amplifier 220.

The atrial sense amplifier 214 and the ventricular sense amplifiers 220 and 222 preferably take the form of automatic gain controlled amplifiers with adjustable sensitivity. In accordance with the invention, ICD 100 and, more specifically, microprocessor 224 maintains the sensitivity of the second ventricular sense amplifier 222 to be lower than that of first ventricular sense amplifier such that second ventricular sense amplifier 222 is able to detect events under-sensed by first ventricular sense amplifier 220. In addition, atrial sense amplifier 214 and first and second ventricular sense amplifiers 220 and 222 receive timing information from pacer timing and control circuitry 226. Specifically, atrial sense amplifier 214 and first and second ventricular sense amplifiers 220 and 222 receive blanking period input, e.g., ABLANK, VBLANK1, and VBLANK2 respectively, which indicates the amount of time the electrodes are "turned off" in order to prevent saturation due to an applied pacing pulse or defibrillation shock. As will be described, the blanking periods first and second ventricular sense amplifiers 220 and 222 and, in turn, the blanking periods of sensing electrodes associated with the respective amplifiers may be automatically adjusted by ICD 100 to reduce the likelihood of sensing cardiac events outside of the desired R-waves (for example, P-waves and T-waves). The general operation of the ventricular sense amplifiers 220 and 222 and the atrial sense amplifier 214 may correspond to that disclosed in U.S. Pat. No. 5,117,824, by Keimel, et al., incorporated herein by reference in its entirety. Whenever a signal received by atrial sense amplifier 214 exceeds an atrial sensitivity, a signal is generated on the P-out signal line. Whenever a signal received by the ventricular sense amplifier 220 exceeds a first ventricular sensitivity, a signal is generated on the $R_{OUT1}$ signal line, and whenever a signal received by the ventricular sense amplifier 222 exceeds a second ventricular sensitivity, a signal is generated on the $R_{OUT2}$ signal line. As described in more detail below, bradycardia or asystole detected based on R-waves sensed by the first ventricular sense amplifier 220 are verified based on whether or not additional R-waves—under-sensed by the first ventricular sense amplifier 220—are sensed by second ventricular sense amplifier 222.

Switch matrix 228 is used to select which of the available electrodes are coupled to a wide band amplifier 230 for use in digital signal analysis. Selection of the electrodes is controlled by the microprocessor 224 via data/address bus 232. The selected electrode configuration may be varied as desired for the various sensing, pacing, cardioversion and defibrillation functions of the ICD 100.

Signals from the electrodes selected for coupling to bandpass amplifier 230 are provided to multiplexer 234, and thereafter converted to multi-bit digital signals by A/D converter 236, for storage in random access memory 238 under control of direct memory access circuit 240 via data/address bus 232. Microprocessor 224 may employ digital signal analysis techniques to characterize the digitized signals stored in random access memory 238 to recognize and classify the patient's heart rhythm employing any of the numerous signal processing methodologies known in the art. In one embodiment (described in more detail with respect to FIGS. 10A-11), EGM data stored in RAM 238 is analyzed in response to bradycardia or asystole detected by first ventricular amplifier 220 to determine whether the detected bradycardia or asystole is appropriate. This embodiment, implemented in firmware, does not require a second sensing channel (i.e., second ventricular amplifier 222). Rather, the stored EGM data is analyzed using a secondary threshold to detect events under-sensed by the first ventricular amplifier 220. Detection and verification of the bradycardia or asystole results in an episode of EGM data, along with sensed intervals and corresponding annotations of sensed events, are preferably stored in random access memory 238.

The telemetry circuit 242 receives downlink telemetry from and sends uplink telemetry to an external programmer, as is conventional in implantable anti-arrhythmia devices, by means of an antenna 244. Data to be uplinked to the programmer and control signals for the telemetry circuit are provided by microprocessor 224 via address/data bus 232. EGM data that has been stored upon arrhythmia detection (i.e., bradycardia or asystole) or as triggered by other monitoring algorithms may be uplinked to an external programmer using telemetry circuit 242. Received telemetry is provided to microprocessor 224 via multiplexer 234. Numerous types of telemetry systems known in the art for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 226 includes programmable digital counters which control the basic time intervals associated with various single, dual or multi-chamber pacing modes or anti-tachycardia pacing therapies delivered in the atria or ventricles. Pacer circuitry 226 also determines the amplitude of the cardiac pacing pulses under the control of microprocessor 224.

During pacing, escape interval counters within pacer timing and control circuitry 226 are reset upon sensing of R-waves or P-waves as indicated by the output of amplifiers 214, 220 and 222, respectively. In accordance with the selected mode of pacing, pacing pulses are generated by atrial pacer output circuit 244 and ventricular pacer output circuit 246. The pacer output circuits 244 and 246 are coupled to the desired electrodes for pacing via switch matrix 228. The escape interval counters are reset upon generation of pacing pulses, and thereby control the basic timing of cardiac pacing functions, including anti-tachycardia pacing. As discussed in more detail with respect to FIGS. 12A-13, a secondary timer may be utilized to verify a detected asystole episode. In particular, in response to a detected asystole by the primary sensing channel, a secondary timer is initialized and the detected asystole is analyzed using a secondary threshold. The secondary timer continues to increment unless an under-sensed event is detected by the secondary threshold, in which case the secondary timer is reset. Following analysis of the detected asystole episode with the secondary threshold, the secondary timer is utilized to determine if the asystole detection was appropriate.

The microprocessor 224 includes associated read-only memory (ROM) in which stored programs controlling the operation of the microprocessor 224 reside. For example, the embodiment described with respect to FIGS. 10A-13, which implements an embodiment of the present invention in firmware, would be implemented with programs stored in the ROM of microprocessor 224. A portion of the random access memory (RAM) 238 may be configured as a number of recirculating buffers capable of holding a series of measured intervals for analysis by the microprocessor 224 for verifying a detected bradycardia or asystole.

In the event that higher voltage cardioversion or defibrillation pulses are required, microprocessor 224 activates the cardioversion and defibrillation control circuitry 248 to initiate charging of the high voltage capacitors 250 and 252 via charging circuit 254 under the control of high voltage charging control line 256. The voltage on the high voltage capacitors is monitored via a voltage capacitor (VCAP) line 258, which is passed through the multiplexer 220. When the voltage reaches a predetermined value set by microprocessor 224, a logic signal is generated on the capacitor full (CF) line 260, terminating charging. The defibrillation or cardioversion pulse is delivered to the heart under the control of the pacer timing and control circuitry 226 by the output circuit 208 via a control bus 262. The output circuit 208 determines the electrodes used for delivering the cardioversion or defibrillation pulse and the pulse wave shape.

Figure 3:
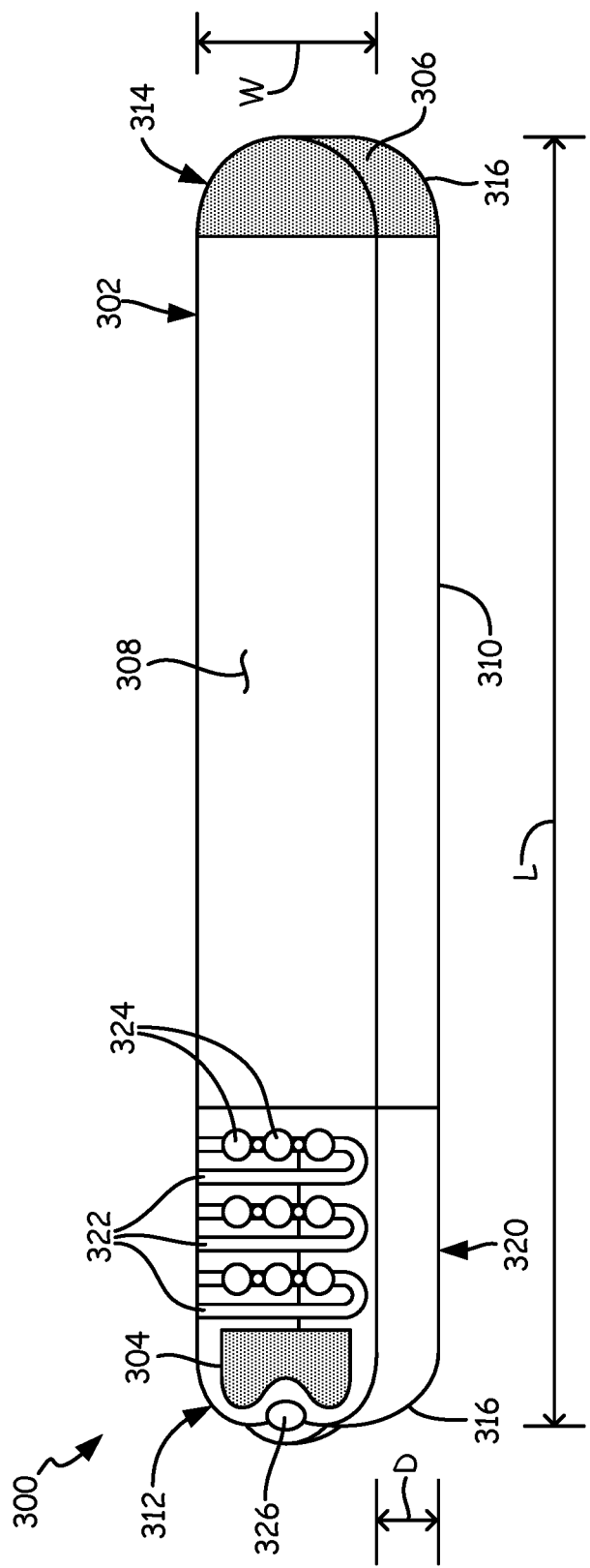
FIG. 3 is a schematic diagram of an exemplary insertable cardiac monitor for detecting a bradycardia/asystole event according to another embodiment of the present disclosure.

FIG. 3 is a conceptual diagram of an example of an insertable cardiac monitor 300 for detecting a bradycardia/asystole event, according to another embodiment of the present disclosure. In the embodiment shown in FIG. 3, insertable cardiac monitor 300 may be embodied as a monitoring device having housing 302, proximal electrode 304 and distal electrode 306. Housing 302 may further comprise first major surface 308, second major surface 310, proximal end 312, and distal end 314. Housing 302 encloses electronic circuitry 400 and power source 402 (shown in FIG. 4) located inside the insertable cardiac monitor 300 and protects the circuitry contained therein from body fluids. Electrical feedthroughs provide electrical connection of electrodes 304 and 306.

In the embodiment shown in FIG. 3, insertable cardiac monitor 300 is defined by a length L, a width W and thickness or depth D and is in the form of an elongated rectangular prism wherein the length L is much larger than the width W, which in turn is larger than the depth D. In one embodiment, the geometry of the insertable cardiac monitor 300—in particular a width W greater than the depth D—is selected to allow the cardiac monitor 300 to be inserted under the skin of the patient using a minimally invasive procedure and to remain in the desired orientation during insert. For example, the device shown in FIG. 3 includes radial asymmetries (notably, the rectangular shape) along the longitudinal axis that maintains the device in the proper orientation following insertion. For example, in one embodiment the spacing between proximal electrode 304 and distal electrode 306 may range from 30 millimeters (mm) to 55 mm, 35 mm to 55 mm, and from 40 mm to 55 mm and may be any range or individual spacing from 25 mm to 60 mm. In addition, insertable cardiac monitor 300 may have a length L that ranges from 30 mm to about 70 mm. In other embodiments, the length L may range from 40 mm to 60 mm, 45 mm to 60 mm and may be any length or range of lengths between about 30 mm and about 70 mm. In addition, the width W of major surface 308 may range from 3 mm to 10 mm and may be any single or range of widths between 3 mm and 10 mm. The thickness of depth D of cardiac monitor device 300 may range from 2 mm to 9 mm. In other embodiments, the depth D of insertable cardiac monitor 300 may range from 2 mm to 5 mm and may be any single or range of depths from 2 mm to 9 mm. In addition, insertable cardiac monitor 300 according to an embodiment of the present invention is has a geometry and size designed for ease of implant and patient comfort. Embodiments of insertable cardiac monitor 300 described in this disclosure may have a volume of three cubic centimeters (cm) or less, 1.5 cubic cm or less or any volume between three and 1.5 cubic centimeters.

In the embodiment shown in FIG. 3, once inserted within the patient, the first major surface 308 faces outward, toward the skin of the patient while the second major surface 310 is located opposite the first major surface 308. In addition, in the embodiment shown in FIG. 3, proximal end 312 and distal end 314 are rounded to reduce discomfort and irritation to surrounding tissue once inserted under the skin of the patient. Insertable cardiac monitor 300, including instrument and method for inserting monitor 300 is described, for example, in U.S. Patent Publication No. 2014/0276928, incorporated herein by reference in its entirety.

As described with other embodiments, proximal electrode 304 and distal electrode 306 are used to sense cardiac signals for determining a bradycardia or asystole event, described below, e.g. ECG signals, intra-thoracically or extra-thoracically, which may be sub-muscularly or subcutaneously. ECG signals may be stored in a memory of the insertable cardiac monitor 300, and ECG data may be transmitted via integrated antenna 322 to another medical device, which may be another implantable device or an external device. In alternative applications, electrodes 304 and 306 may be used for sensing any bio-potential signal of interest, which may be, for example, an EGM, EEG, EMG, or a nerve signal, from any implanted location.

In the embodiment shown in FIG. 3, proximal electrode 304 is in close proximity to the proximal end 312 and distal electrode 306 is in close proximity to distal end 314. In this embodiment, distal electrode 306 is not limited to a flattened, outward facing surface, but may extend from first major surface 308 around rounded edges 316 and/or end surface 318 and onto the second major surface 310 so that the electrode 306 has a three-dimensional curved configuration. In the embodiment shown in FIG. 3, proximal electrode 304 is located on first major surface 308 and is substantially flat, outward facing. However, in other embodiments proximal electrode 304 may utilize the three dimensional curved configuration of distal electrode 306, providing a three dimensional proximal electrode (not shown in this embodiment). Similarly, in other embodiments distal electrode 306 may utilize a substantially flat, outward facing electrode located on first major surface 308 similar to that shown with respect to proximal electrode 304. The various electrode configurations allow for configurations in which proximal electrode 304 and distal electrode 306 are located on both first major surface 308 and second major surface 310. In other configurations, such as that shown in FIG. 3, only one of proximal electrode 304 and distal electrode 306 is located on both major surfaces 308 and 310, and in still other configurations both proximal electrode 304 and distal electrode 306 are located on one of the first major surface 308 or the second major surface 310 (i.e., proximal electrode 304 located on first major surface 308 while distal electrode 306 is located on second major surface 310). In another embodiment, cardiac monitor device 300 may include electrodes on both major surface 308 and 310 at or near the proximal and distal ends of the device, such that a total of four electrodes are included on cardiac monitor device 300. Electrodes 304 and 306 may be formed of a plurality of different types of biocompatible conductive material, e.g. stainless steel, titanium, platinum, iridium, or alloys thereof, and may utilize one or more coatings such as titanium nitride or fractal titanium nitride.

In the embodiment shown in FIG. 3, proximal end 312 includes a header assembly 320 that includes one or more of proximal electrode 304, integrated antenna 322, anti-migration projections 324, and/or suture hole 326. Integrated antenna 322 is located on the same major surface (i.e., first major surface 308) as proximal electrode 304 and is also included as part of header assembly 320. Integrated antenna 322 allows insertable cardiac monitor 300 to transmit and/or receive data. In other embodiments, integrated antenna 322 may be formed on the opposite major surface as proximal electrode 304, or may be incorporated within the housing 322 of insertable cardiac monitor 300. In the embodiment shown in FIG. 3, anti-migration projections 324 are located adjacent to integrated antenna 322 and protrude away from first major surface 308 to prevent longitudinal movement of the device. In the embodiment shown in FIG. 3, anti-migration projections 324 includes a plurality (e.g., nine) small bumps or protrusions extending away from first major surface 308. As discussed above, in other embodiments anti-migration projections 324 may be located on the opposite major surface as proximal electrode 304 and/or integrated antenna 322. In addition, in the embodiment shown in FIG. 3 header assembly 320 includes suture hole 326, which provides another means of securing insertable cardiac monitor 300 to the patient to prevent movement following insert. In the embodiment shown, suture hole 326 is located adjacent to proximal electrode 304. In one embodiment, header assembly 320 is a molded header assembly made from a polymeric or plastic material, which may be integrated or separable from the main portion of insertable cardiac monitor 300.

Figure 4:
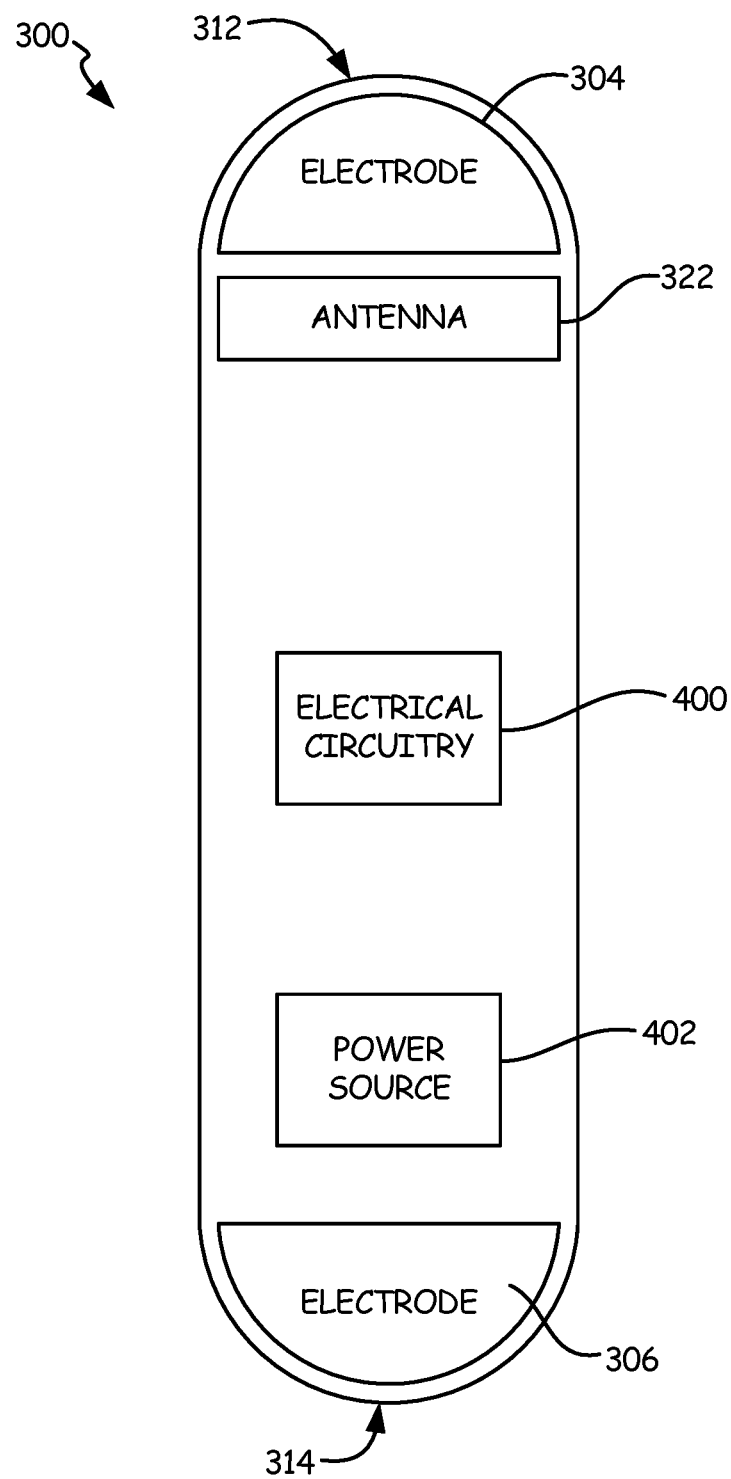
FIG. 4 is a conceptual diagram of an example of an exemplary insertable cardiac monitor for detecting a bradycardia/asystole event according to another embodiment of the present disclosure.

FIG. 4 is a functional schematic diagram of the insertable cardiac monitor 300 as shown in FIG. 3 according to an embodiment of the present disclosure. Insertable cardiac monitor 300 includes housing 302, proximal electrode 304 located at proximal end 312, distal electrode 306 located at distal end 314, integrated antenna 322, electrical circuitry 400 and power source 402. In particular, electrical circuitry 400 is coupled to proximal electrode 304 and distal electrode 306 to sense cardiac signals and monitor events, including bradycardia and asystole as described in more detail below. Electrical circuitry 400 is also connected to transmit and receive communications via integrated antenna 322. Power source 402 provides power to electrical circuitry 400, as well as to any other components that require power. Power source 402 may include one or more energy storage devices, such as one or more rechargeable or non-rechargeable batteries. The insertable cardiac monitor 300 as shown in FIGS. 3 and 4 is a monitoring-only device. However, in other examples, insertable cardiac monitor 300 may further provide therapy delivery capabilities as described with respect to FIGS. 1-2.

In the embodiment shown in FIG. 4, electrical circuitry 400 receives raw EGM signals monitored by proximal electrode 304 and distal electrode 306. Electrical circuitry 400 includes components/modules for converting the raw EGM signal to a processed EGM signal that can be analyzed to detect sense events. Although not shown, electrical circuitry 400 may include any discrete and/or integrated electronic circuit components that implement analog and/or digital circuits capable of producing the functions described for analyzing EGM signals to detect/verify bradycardia and/or asystole events. For example, the electrical circuitry 400 may include analog circuits, e.g., pre-amplification circuits, filtering circuits, and/or other analog signal conditioning circuits (such as those shown with respect to FIG. 2). The modules may also include digital circuits, e.g., digital filters, combinational or sequential logic circuits, state machines, integrated circuits, a processor (shared, dedicated, or group) that executes one or more software or firmware programs, memory devices, or any other suitable components or combination thereof that provide the described functionality.

In one embodiment electrical circuitry 400 includes a sensing unit for monitoring the EGM signal detected by the respective proximal and distal electrodes 304 and 306, respectively, and at least a primary sensing channel that utilizes a first threshold for sensing events in the EMG signal. Sensed events (e.g., R-waves) are utilized to detect at least one of bradycardia or asystole episodes. In one embodiment, electrical circuitry 400 includes a processor is utilized to receive information regarding the sensed events and implements one or more algorithms for determining whether a bradycardia/asystole event has occurred. In addition, electrical circuitry 400 may further include a secondary channel and/or threshold used to detect sense events under-sensed by the first threshold. The results of which are utilized (for example, by the processor) to verify the bradycardia sense or asystole sense. In addition, the analog voltage signals received from electrodes 304 and 306 may be passed to analog-to-digital (A/D) converters included in the electrical circuitry 400, and stored in a memory unit (not shown) included as part of electrical circuitry 400 for subsequent analysis with firmware executed by the processor included as part of electrical circuitry 400. This additional analysis may also include comparison of the EGM signal to a secondary threshold to detect sense events under-sensed by the first threshold.

Electrical circuitry 400 controls insertable cardiac monitor 300 functions and processes EGM signals received from electrodes 304 and 306 according to programmed signal analysis routines or algorithms. The insertable cardiac monitor 300 may include other optional sensors (not shown) for monitoring physiological signals, such as an activity sensor, pressure sensor, oxygen sensor, accelerometer, or other sensor used to monitor a patient. These may also be provided to electrical circuitry 400 for processing.

Electrical circuitry 400 may similarly control monitoring time intervals and sampling rates according to a particular clinical application. In addition, electrical circuitry may include state machines or other sequential logic circuitry to control device functions and need not be implemented exclusively as a microprocessor. For example, electrical circuitry 400 may include timers utilized to detect asystole events as described in more detail below.

Electrical circuitry 400 communicates with integrated antenna 322 (shown in FIG. 3) to transmit electrical signal data, e.g. ECG signal data, stored in memory or received from electrical circuitry 400 in real time. Antenna 322 may be configured to transmit and receive communication signals via inductive coupling, electromagnetic coupling, tissue conductance, Near Field Communication (NFC), Radio Frequency Identification (RFID), BLUETOOTH®, WiFi, or other proprietary or non-proprietary wireless telemetry communication schemes. Communication module enables the insertable cardiac monitor 300 to communicate with a programmer (not shown) located external to the device 300 and includes a user interface that presents information to and receives input from a user. It should be noted that the user may also interact with programmer remotely via a networked computing device.

A user, such as a physician, technician, surgeon, electrophysiologist, other clinician, or patient, interacts with programmer to communicate with insertable cardiac monitor 300. For example, the user may interact with programmer to retrieve physiological or diagnostic information from cardiac monitor 300. A user may also interact with programmer to program cardiac monitor 300, e.g., select values for operational parameters of the cardiac monitor 300. For example, the user may use programmer to retrieve information from cardiac monitor 300 regarding the rhythm of a patient heart, trends therein over time, or arrhythmic episodes. Cardiac monitor 300 and the programmer may communicate via wireless communication using any techniques known in the art.

Depiction of different features as modules is intended to highlight different functional aspects and does not necessarily imply that such modules must be realized by separate hardware or software components. Rather, functionality associated with one or more modules may be performed by separate hardware, firmware and/or software components, or integrated within common hardware, firmware and/or software components.

Inappropriate Bradycardia Detection

Figure 5:
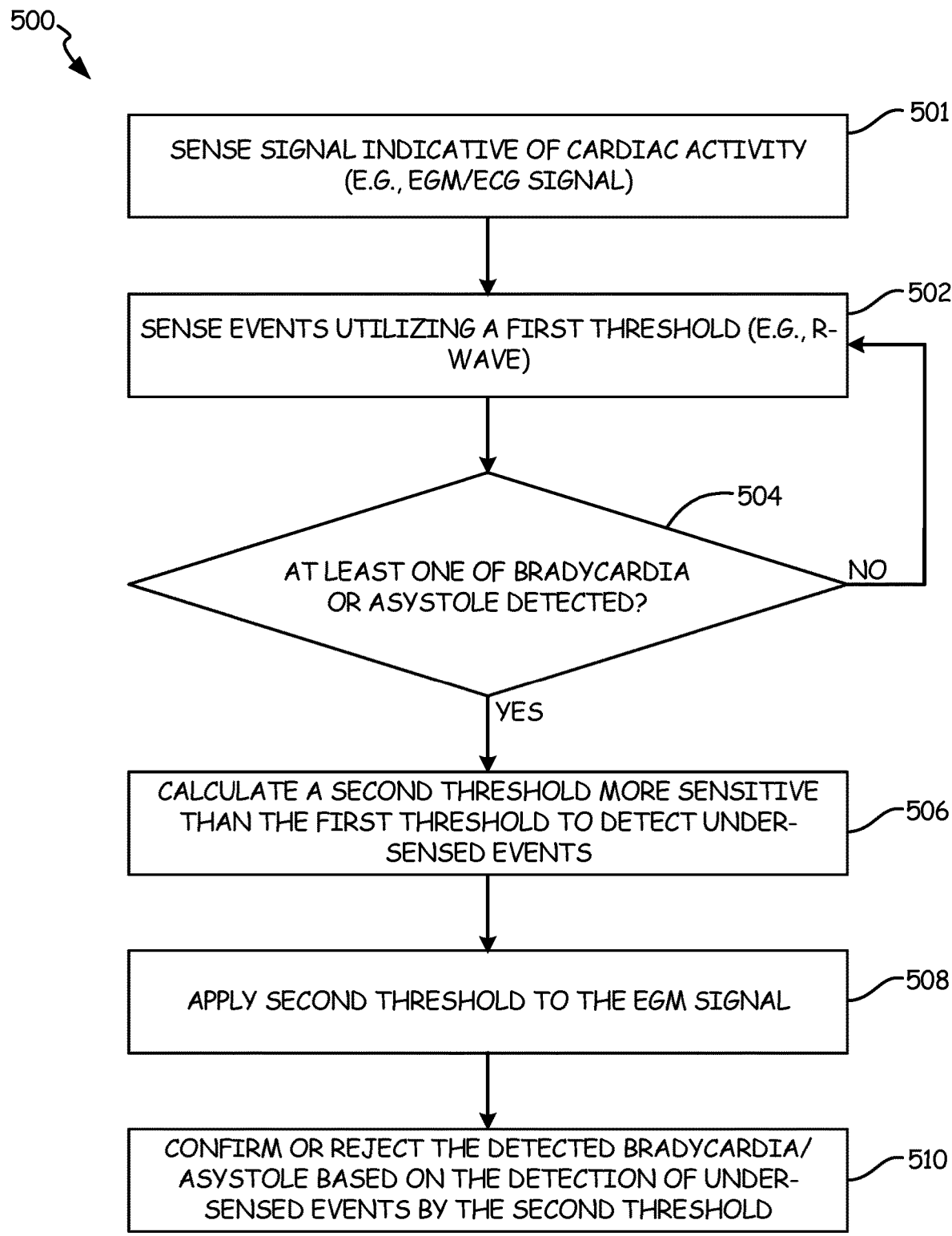
FIG. 5 is a flowchart of a method of detecting and validating bradycardia/asystole events according to an embodiment of the present invention.

As discussed above, the presence of irregular cardiac (specifically ventricular) depolarizations such as premature ventricular contractions (PVCs) can lead to the under-sensing of events by the detection methods typically employed by monitoring devices. The under-sensing of events results in the monitoring system incorrectly identifying bradycardia or asystole events. FIG. 5 describes a method and system for verifying bradycardia and/or asystole episodes based on the detection of under-sensed events. FIGS. 6-11 describe a method and system for detecting inappropriate bradycardia specifically, and FIGS. 12A-13 describe a method and system for detecting inappropriate asystole specifically.

FIG. 5 is a flowchart of method 500 of detecting and validating bradycardia and asystole episodes according to an embodiment of the present invention. At step 501, signals indicative of cardiac activity (e.g., electrogram (EGM), electrocardiogram (ECG), etc.) are sensed. As described with respect to FIGS. 1-4, a plurality of device/electrode configurations may be utilized to monitor EGM/ECG signals. At step 502, sense events (e.g., R-waves) are detected utilizing a first channel/threshold. For example, in one embodiment an R-wave is sensed each time the monitored electrogram (EGM) signal exceeds a first threshold. As described in more detail with respect to FIGS. 6A and 6B, the first threshold utilized at step 502 may be an auto-adjusted threshold that varies based on one or more factors to avoid oversensing events in the EGM signal, such as T-waves and P-waves.

At step 504, the interval between sensed events—including both R-waves and escape beats—are utilized to detect at least one of bradycardia or asystole episodes. For example, a bradycardia sense is detected if the interval between successive R-waves (i.e., the R-R interval) is greater than a bradycardia interval. Consecutive detection of bradycardia sense for a number of beats (e.g., four) leads to a bradycardia episode detection. Likewise, an asystole episode may be detected based on a longer interval between sensed events (which may include an escape beat). If no bradycardia or asystole is detected at step 504, then the method continues at step 501 with monitoring of cardiac activity. However, if a bradycardia sense or asystole episode is detected, then the method continues at steps 506-510 to determine whether the detection of bradycardia/asystole episode is appropriate.

In particular, at step 506 a second threshold is calculated/selected to detect events that may have been under-sensed by the first threshold. The second threshold is therefore calculated and/or selected to be more sensitive than the first threshold. As discussed in more detail below, the second threshold may be calculated in a variety of ways. In one embodiment, the second threshold is calculated based on the amplitude of sensed events. In each case, however, the purpose of the second threshold is to detect events under-sensed by the first threshold.

At step 508 the second threshold is applied to the EGM segment that resulted in the bradycardia or asystole detection. Previously under-sensed events are detected in response to the EGM signal exceeding the second threshold value. At step 510, the detected bradycardia or asystole episode is either confirmed or rejected based on events detected via application of the second threshold. For example, if an event under-sensed by the first threshold is sensed by the second threshold, and the under-sensed event results in no R-R interval being greater than the bradycardia interval, then the bradycardia sense event is rejected. Conversely, if either no under-sensed events are detected, or despite detection of under-sensed events the R-R interval remains greater than the bradycardia interval, the bradycardia sense event is confirmed.

Figure 6:
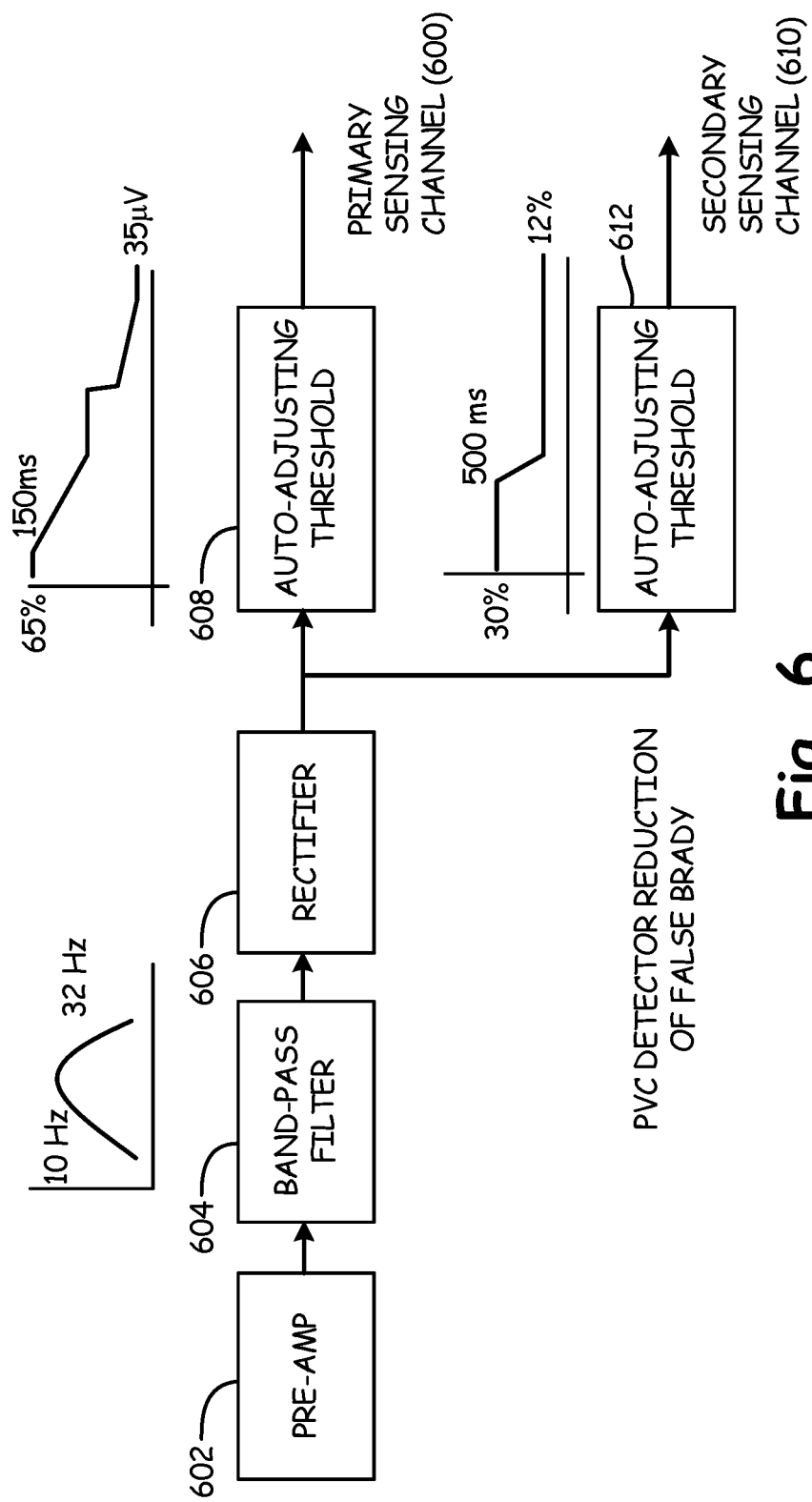
FIG. 6 is a functional schematic diagram of an embodiment that utilizes first and second channels to detect and validate bradycardia/asystole events according to an embodiment of the present invention.

FIG. 6 is a functional schematic diagrams illustrating implementation of dual sense channels according to embodiments of the present invention. In the embodiment shown in FIG. 6, first sensing channel 600 includes pre-amplifier 602, band-pass filter 604, rectifier 606, and auto-adjusting threshold 608, while secondary sensing channel 610 includes second auto-adjusting threshold 612. A raw EGM signal measured by one or more electrodes is provided as an input to pre-amplifier 602. The combination of pre-amplifier, band-pass filter 604, and rectifier 606 act to filter and rectify the raw EGM signal to reduce noise and improve the quality of the EGM signal. The filtered/rectified EGM signal is provided to first auto-adjusting threshold 608. Events (e.g., R-waves) are sensed in response to the received filtered/rectified EGM signal exceeding the value of the first auto-adjusting threshold. To avoid noise or other artifacts from triggering the sensing of an R-wave, the auto-adjusting threshold 608 decays from a maximum value following a previous R-wave sense to a minimum or floor value. A graphical representation of the first auto-adjusting threshold 608 according to an embodiment of the present invention is illustrated in the region above auto-adjusting threshold box 608. In the embodiment shown in FIG. 6, the auto-adjusting threshold 608 is set to a value related to the amplitude of the previously sensed R-wave (e.g., 65% of the previous amplitude), although in other embodiments this may be a predetermined value. The auto-adjusting threshold 608 then decays gradually to a minimum or floor value (e.g., 35 µV). Although the first auto-adjusting threshold 608 is designed and optimized to correctly sense typical R-wave depolarizations, in particular to avoid T-wave over-sensing, certain types of events such as PVCs may not be properly sensed by the first auto-adjusting threshold 608 (a condition referred to as "under-sensing"). The under-sensing of these events may result in an R-R interval (i.e., the interval between consecutively sensed R-waves) that indicates the patient is experiencing a bradycardia.

The secondary sensing channel 610 comprised of secondary auto-adjusting threshold 612 is utilized validate (i.e., reject or accept) the detection of bradycardia/asystole episodes by primary sensing channel 600. In particular, secondary sensing channel 610 acts to detect those events under-sensed by primary sensing channel 600. In the embodiment shown in FIG. 6, secondary auto-adjusting threshold 612 also decays from a maximum value to a minimum value or floor. In particular, the secondary auto-adjusting threshold 612 is designed to decay quickly to allow for events such as PVCs to be detected. In the embodiment shown in FIG. 6, the maximum value of the auto-adjusting threshold 612 is related to the amplitude of the previously sensed event (e.g., 30% of the sensed amplitude). As compared with first auto-adjusting threshold 608, the maximum value of secondary auto-adjusting threshold 612 is lower, and is therefore more sensitive to under-sensed events. Following a blanking period, the secondary auto-adjusting threshold 612 decays rapidly to the minimum or floor value. In the embodiment shown in FIG. 6, the floor value is related to the amplitude of the previously sensed event (e.g., 12%), however, in other embodiments this value may be predetermined or programmable. In one embodiment, even if the floor value is related to the amplitude of the previously sensed event (e.g., 12%), the floor value cannot decrease to a value less than the floor value utilized by primary auto-adjusting threshold 608. In the embodiment shown in FIG. 6, the secondary auto-adjusting threshold 612 decays more rapidly to a minimum or floor value as compared with the primary auto-adjusting threshold, which also improves the secondary auto-adjusting threshold 612 sensitivity to under-sensed events. A blanking period may be utilized to maintain the secondary auto-adjusting threshold 612 at the maximum value for period of time, which may be predetermined or programmable (e.g., 500 ms in the embodiment shown in FIG. 6). The blanking period prevents sensing events such as T-waves that immediately follow R-wave senses.

In the embodiment shown in FIG. 6, a plurality of parameters define the behavior of the secondary auto-adjusting threshold 612. These parameters may be programmable and may be stored in hardware and/or software. In one embodiment these parameters include the maximum value of the auto-adjust threshold (e.g., 30% of previously sense R-wave amplitude), duration of the blanking period following an R-wave sense before the threshold begins to decrease or decay (e.g., 500 ms), the rate at which the threshold decreases or decays, and the minimum threshold value or floor. In one embodiment, the maximum value is not allowed to exceed a maximum value (i.e., is clipped to a maximum value), which may also be programmable.

The output of primary sensing channel 600 and secondary sensing channel 610 are utilized to determine whether a detected bradycardia/asystole episode was appropriate or not. In one embodiment, a processor (e.g., microprocessor 224 in FIG. 2, or processing and control unit 404 in FIG. 4) combines the outputs of primary sensing channel 600 and secondary sensing channel 610 and determines whether the detected bradycardia/asystole was appropriate. For example, RR intervals determined by dual channel sensing as not indicative of a bradycardia sense should be less than the bradycardia interval and greater than 200 ms (typical value of PR interval to avoid p-wave undersensing).

FIG. 7A illustrates an electrogram (EGM) signal 700. FIG. 7B illustrates processing of the filtered and rectified EGM signal 702 by primary sensing channel and resulting bradycardia detect, and FIG. 7C illustrates processing of the EGM signal within a second channel to verify/reject the detected bradycardia according to an embodiment of the present invention. With respect to FIG. 7A, the various types of sensed events (e.g., R-waves, PVCs) are labeled to aid in understanding how under-sensing of events by the primary sense channel results in improper bradycardia detection. In the example shown in FIG. 7A, the raw EGM signal is characterized by bigeminal PVC beats. For example, R-waves $R_3$ and $R_4$ are separated by a PVC beat ($PVC_1$). Likewise, R-waves $R_4$ and $R_5$ are separated by $PVC_2$. This pattern continues with alternating R-waves and PVC beats.

FIG. 7B illustrates comparison of the filtered/rectified EGM signal 702 (solid black line) with the primary auto-adjusting threshold 706 described with respect to FIG. 6. In this example, the filtered/rectified R-waves are characterized by amplitudes higher than those of the filtered/rectified PVC beats. This is due, in part, to the lower-frequency content (i.e., wider QRS complex shape) of the PVC beats, which when filtered results in a lower amplitude filtered/rectified EGM signal. As a result of this lower amplitude, the embodiment shown in FIG. 7B illustrates how the primary sensing threshold fails to detect the presence of the PVC beats (i.e., the PVC beats are under-sensed). For example, following the sense of R-wave $R_3$, the primary sensing threshold is reset to a maximum value, and after a brief period of time begins decaying toward a minimum or floor value. However, the rate of the decay is not fast enough to detect the presence of $PVC_1$. The same scenario occurs with respect to other PVC beats, with each of $PVC_1$, $PVC_2$, $PVC_3$, $PVC_4$, $PVC_5$, and $PVC_6$ being under-sensed. As a result of the under-sensing of $PVC_1$, the R-R interval 710 measured between R-waves $R_3$ and $R_4$ is greater than the bradycardia interval, which results in an erroneous bradycardia sense (and possible erroneous detection of a bradycardia episode if a plurality of inappropriate bradycardia senses are detected).

FIG. 7C illustrates how the erroneous bradycardia detection shown in FIG. 7B is remedied by the secondary auto-adjust sensing threshold 708. Notice that in response to each sensed event, secondary auto-adjust sensing threshold is reset to a maximum value that is related to the magnitude of the previously sensed event. The secondary auto-adjust sensing threshold 708 remains at the maximum value for a period of time (i.e., predetermined blanking period) before decreasing or decaying rapidly to a minimum or floor value. For example, following the sense of R-wave $R_3$, the secondary auto-adjust threshold is reset to a maximum value that is approximately 30% of the magnitude of the sensed R-wave. The secondary auto-adjust threshold 708 remains at this maximum value for the duration of a blanking period before decreasing rapidly to a minimum or floor value. As shown, the fast (relative to the first auto-adjust threshold) decay of the threshold value results in PVC beat $PVC_1$ being sensed. A determination is made regarding whether the interval between $PVC_1$ and $R_4$ (labeled 712) is greater than the bradycardia threshold. If it is not, then the bradycardia sense with respect to the primary sense channel is discarded. As shown with respect to the remainder of the EGM signal, PVC beats are successfully detected, thereby preventing erroneous bradycardia senses with respect to these beats as well (assuming the resulting intervals are less than the bradycardia interval).

Figure 8:
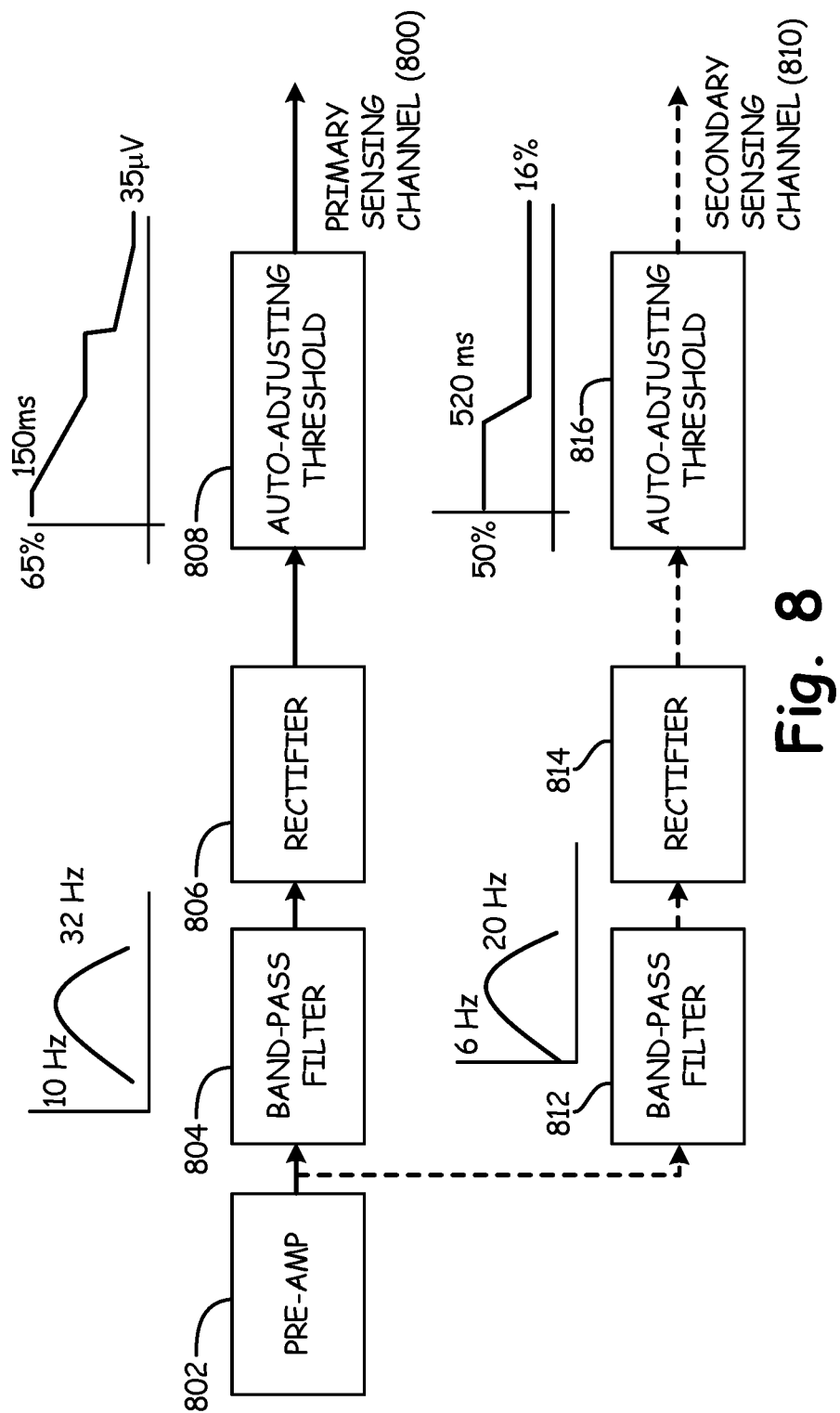
FIG. 8 is a functional schematic diagram of an embodiment that utilizes first and second channels to detect and validate bradycardia/asystole events according to another embodiment of the present invention.

FIG. 8 is a functional schematic diagrams illustrating implementation of dual sense channels according to another embodiments of the present invention. In the embodiment shown in FIG. 8, first sensing channel 800 once again includes pre-amplifier 802, band-pass filter 804, rectifier 806, and primary auto-adjusting threshold 808. However, in contrast with the embodiment shown in FIG. 6, secondary sensing channel 810 includes a second band-pass filter 812, second rectifier 814, and secondary auto-adjusting threshold 816.

In the embodiment shown in FIG. 8, primary sensing channel 800 operates in the same way as primary sensing channel 600 described with respect to FIG. 6. Primary sensing channel 800 comprises pre-amplifier 802, band-pass filter 804, rectifier 806, and auto-adjusting threshold 808 utilized to detect sense events (e.g., R-waves) based on a monitored EGM signals. Secondary sensing channel 810, however, utilizes a separate band-pass filter 812 and rectifier 814 used to filter/rectify the raw EGM signal. In the embodiment shown in FIG. 8, the band-pass filter is designed to target/accentuate lower frequency components (e.g., 6 Hz to 20 Hz) than those targeted by first band-pass filter 804 (e.g., 10 Hz to 32 Hz). As described above with respect to FIG. 7B, PVC beats typically include lower frequency components (i.e., wider QRS complex) than typical r-waves. In this way, the filtered/rectified EGM signal generated by band-pass filter 812 and rectifier 814 will accentuate (convert to higher magnitudes) PVC beats as well as other beats with lower frequency components (wide-complex QRS).

Secondary auto-adjusting threshold 816 is designed to take advantage of the filtered/rectified EGM signal generated by band-pass filter 812 and rectifier 814. For example, because band-pass filter 812 is designed to accentuate lower frequency content such as those associated with PVCs, secondary auto-adjusting threshold 816 may be programmed with a maximum level that is greater than that employed by secondary auto-adjusting threshold 612 (shown in FIG. 6). Similarly, the programmed minimum value or floor utilized in secondary auto-adjusting threshold 816 may be greater than that utilized by second auto-adjusting threshold 612. In this way, secondary sensing channel 810 is utilized to detect events under-sensed by primary sensing channel 800.

In one embodiment, the combination of second band-pass filter 812, second rectifier 814 and secondary auto-adjusting threshold 816 allows for the detection of T-waves by secondary sensing channel 810. In general, T-waves are typically lower in frequency than R-waves, and thus the lower band of frequencies selected by band-pass filter 812 accentuates the T-wave component and makes it easier to sense. A benefit of sensing T-waves (in addition to R-waves), is that the sensed T-waves may be utilized to measure the QT interval (time between a detected QRS complex and a detected t-wave). For example, the location of the T-wave can be determined as the point when the filtered rectified amplitude is at a maximum value in a later portion of the blanking window of the secondary sense channel.

Figure 9:
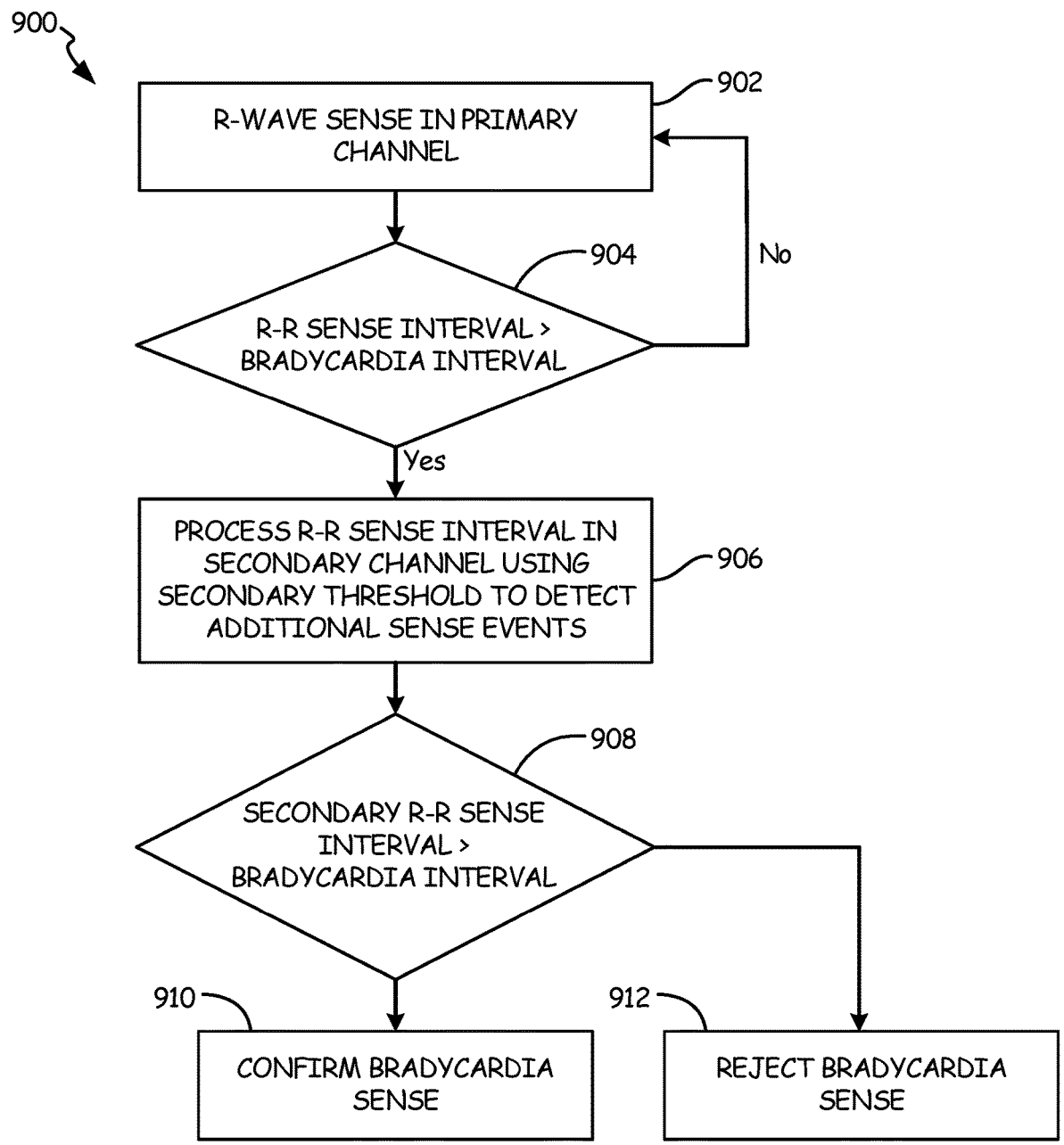
FIG. 9 is a flowchart of a method of detecting and validating bradycardia detections utilizing a first and second channel according to an embodiment of the present invention.

FIG. 9 is a flowchart of a method 900 of detecting and validating bradycardia detections utilizing a first and second channel according to an embodiment of the present invention. The method described with respect to FIG. 9 may be implemented, for example, by either of the dual channel sensing systems described with respect to FIGS. 6 and 8.

At step 902, a sense event (e.g., R-wave) is sensed in the primary channel. As described with respect to FIGS. 6 and 8, a filtered/rectified EGM signal is compared to a threshold value such as an auto-adjusting threshold value to detect R-waves.

At step 904, the interval between sensed R-waves (i.e., R-R interval) is compared to a bradycardia threshold. If the R-R interval is less than the bradycardia threshold, then the patient's heart rate is faster than that indicative of a bradycardia and the sensing of R-waves continues at step 902. If the R-R interval is greater than the bradycardia threshold, then the R-R segment is identified as a bradycardia event. For example, in some embodiments, the second R-wave in the R-R segment is labeled as a bradycardia beat. In other embodiments, the second-wave in the R-R segment is not labeled until after the detected bradycardia has been verified by the second channel. If a bradycardia event is detected at step 904, then the method continues at step 906.

At step 906, the R-R sense interval that led to the bradycardia sense event is processed using the secondary channel. It should be noted that while the steps are ordered in ascending numerical order, this does not require that the steps be performed in this order. In one embodiment, processing of the R-R interval is always performed by the secondary channel contemporaneously with processing performed in the primary channel. However, events sensed in the secondary sensing channel are only utilized if a bradycardia is detected in the primary sensing channel. However, in other embodiments the R-R interval may be stored to a buffer or memory in response to a detected bradycardia sense event, and the stored EGM is subsequently processed by the secondary sensing channel to verify the bradycardia event.

As described with respect to FIGS. 6 and 8, the secondary channel may include a separate, secondary auto-adjust threshold that is utilized to detect additional events within the R-R interval, or may additionally include hardware to filter/rectify the EGM signal before applying a secondary threshold. In particular, as discussed above, the secondary channel is configured to detect irregular beats that were under-sensed by the primary channel, such as PVC beats as well as wide QRS complex beats.

At step 908, based on events sensed by the secondary channel, measured R-R intervals are compared to the bradycardia threshold to determine whether the bradycardia detected at step 904 should be rejected or confirmed. If no additional events were sensed by the secondary channel within the R-R interval, then the R-R interval will remain unchanged and the bradycardia event detected at step 904 is confirmed at step 910. However, if additional sense events are sensed by the secondary channel, and the resulting R-R interval is less than the bradycardia interval then the bradycardia sense event detected at step 904 is rejected at step 912 as inappropriate.

FIGS. 10A-10C and 11 illustrate another method utilized to detect bradycardia events that utilizes a secondary threshold to verify a bradycardia event detected in the first channel. In particular, the method described with respect to FIGS. 10A-10C and 11 are well-suited for implementation in firmware. For example, with respect to the embodiment shown in FIG. 2, firmware included as part of microprocessor 224 may programmed to implement the described method. In other embodiments, the method may be implemented in hardware, software, or a combination thereof.

Figure 10A:
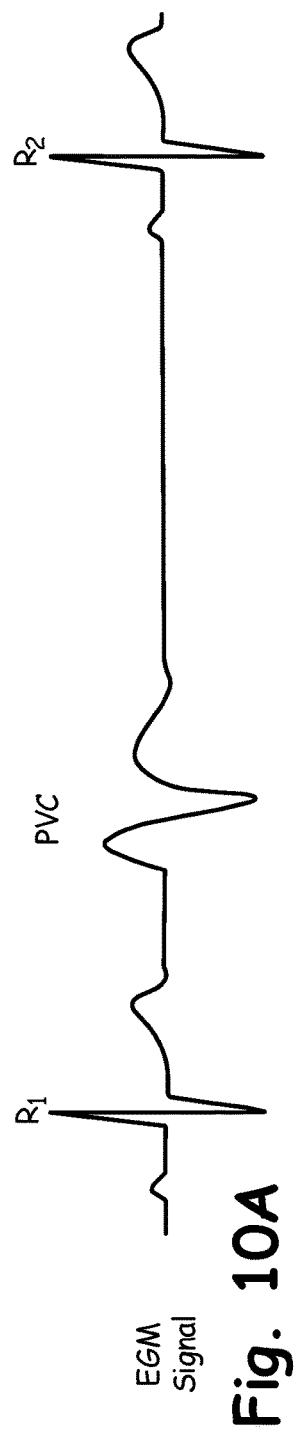
FIG. 10B illustrates analysis of the example EGM signal in a first channel and resulting under-sensing of the PVC beat.
FIG. 10C illustrates analysis of the example EGM signal using a secondary threshold to detect the under-sensed PVC beat.
Figure 10B:
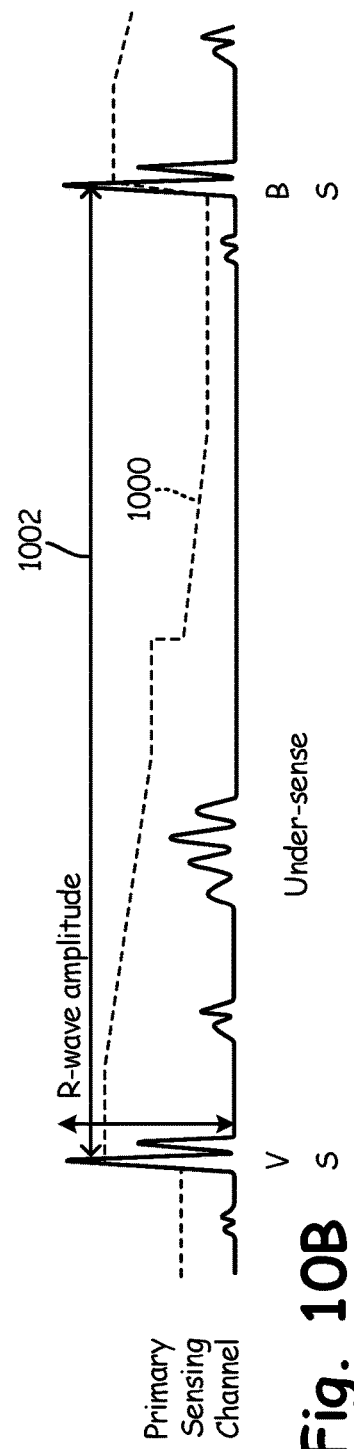

In particular, FIG. 10A illustrates a raw (i.e., unfiltered) electrogram (EGM) signal. In the example shown in FIG. 10A, a R-wave $R_1$ is followed by a PVC beat, and then another R-wave $R_2$. FIG. 10B illustrates the filtered/rectified EGM signal (solid black line) as compared with the first auto-adjust threshold 1000 (dashed line). Once again, filtering/rectifying of the EGM signal results in the higher frequency R-waves having higher amplitudes than the lower frequency PVC beats. As a result, the first auto-adjust threshold 1004 reset in response to the sense of R-wave $R_1$ under-senses the PVC beat (i.e., the PVC beat does not exceed the first auto-adjust threshold 1000, and therefore is not detected). The resulting R-R interval sensed by the primary sense channel (denoted interval 1002) is greater than a bradycardia threshold, and therefore results in detection of a bradycardia event (denoted by the label 'B S' underneath R-wave R2.

Figure 10C:
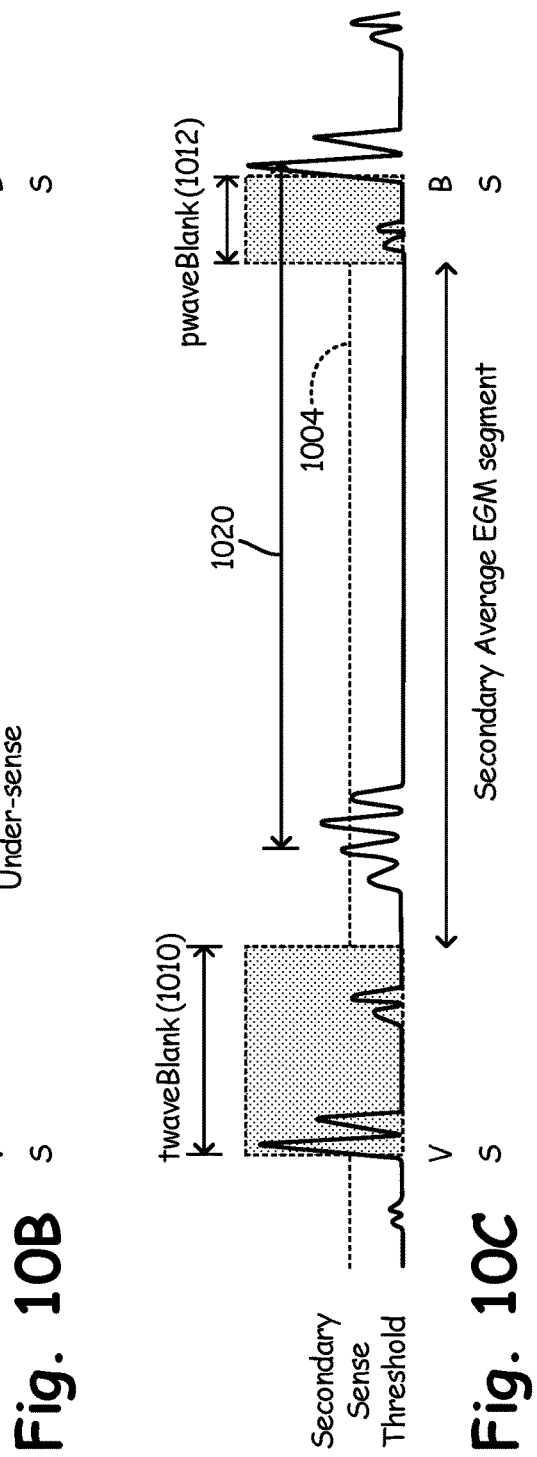

FIG. 10C illustrates utilization of a secondary sense threshold 1004 (dashed line) to confirm or reject the bradycardia detection made by the primary sensing channel. In contrast with the embodiment shown in FIGS. 6 and 8, the embodiment shown in FIG. 10C is most likely to be implemented by firmware, in which following detection of bradycardia event in the first sensing channel, the corresponding EGM segment is stored to a buffer or memory (e.g., RAM 226 shown in FIG. 1) and then subsequently processed retrospectively as shown in FIG. 10C. In one embodiment, a four-point moving average filter is applied to the EGM segment, after taking a single point difference of the raw EGM, that extends from the previous sense to the current sense (i.e., the R-R interval identified as a bradycardia event) to obtain an averaged EGM segment. In addition, blanking periods are extracted from the EGM segment to prevent sensing events within the blanking periods. In the embodiment shown in FIG. 10C, T-wave blanking period 1010 extends for a period of time from the previous R-wave sense, while P-wave blanking period 1012 extends for a period of time preceding the subsequent R-wave sense. The purpose of T-wave blanking period 1010 is to prevent sensing T-waves occurring shortly thereafter a detected R-wave (e.g., R-wave R1). Similarly, the purpose of P-wave blanking period 1012 is to prevent the sensing of P-waves that precede the subsequently detected R-wave (e.g., R-wave R2). Typically, T-wave blanking period 1010 will extend for a longer duration of time than P-wave blanking period 1012. Secondary sense threshold 1004 is calculated/selected that will be used to detect additional sense events within the secondary average EGM segment (i.e., the portion of the EGM segment that extends from the end of T-wave blanking period 1010 to the start of the P-wave blanking period 1012). In one embodiment, the magnitude of the secondary sense threshold 1016 is a function of the amplitude of the previously sensed R-wave (e.g., 30-65% of the magnitude of R-wave R1). In one embodiment, the secondary sense threshold 1004 is a function of the amplitude of the previously sensed R-wave unless the amplitude of the sensed R-wave is less than a selected value (e.g., 100 µV), in which case the secondary sense threshold 1004 is assigned a programmable value (e.g., half of the nominal value or 50 µV).

The EGM segment—minus the blanking periods—is then compared to the secondary sense threshold 1004 to detect events under-sensed by the primary sense channel. In the embodiment shown in FIG. 10C, the portion of the filtered/rectified EGM signal representing the PVC beat crosses the secondary sense threshold 1004 and is therefore detected. As a result of the detected PVC beat, and resulting R-R interval 1020 being less than the bradycardia threshold, the bradycardia event detected by the primary sense channel is rejected.

Figure 11:
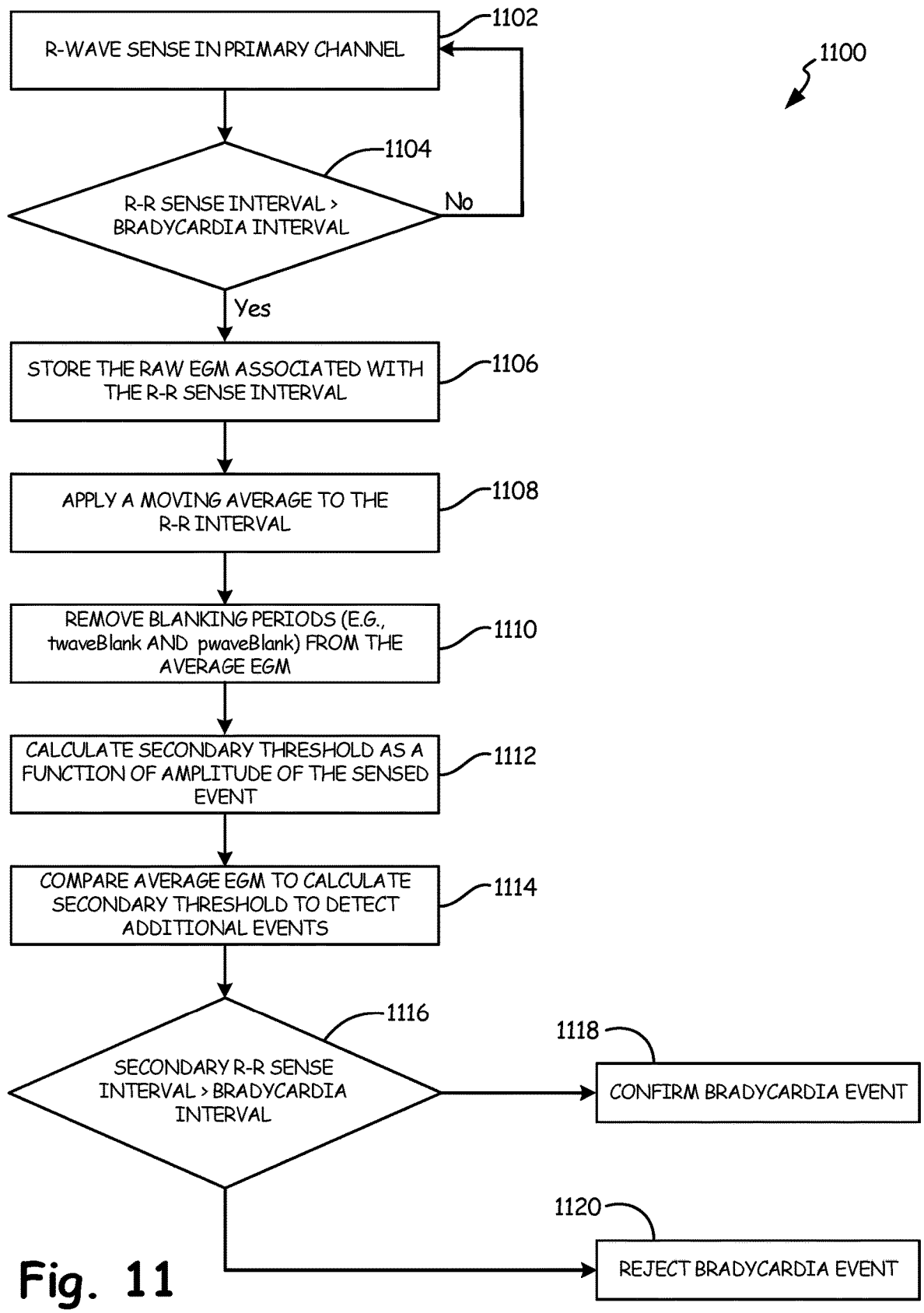
FIG. 11 is a flowchart of a method of detecting and validating bradycardia detections utilizing a secondary threshold according to an embodiment of the present invention.

FIG. 11 is a flowchart of a method 1100 of detecting and validating bradycardia detections utilizing a secondary threshold according to an embodiment of the present invention. At step 1102, R-wave sensing in the primary channel allows an R-R interval to be determined. At step 1104, the R-R interval is compared to the bradycardia threshold. If the R-R interval sensed by the primary channel is not greater than the bradycardia threshold, then no bradycardia event is detected and normal sensing in the primary channel continues at step 1102. If the R-R interval sensed in the primary channel is greater than the bradycardia threshold, then a bradycardia event is detected and the method continues to steps 1106-1120 to either verify or reject the bradycardia sense event.

At step 1106, the EGM associated with the R-R sense interval that resulted in the bradycardia detection is stored to a buffer or memory. In one embodiment, the stored EGM segment is the raw EGM signal. In other embodiments, different forms of filtered and/or rectified EGM segments are stored to the buffer or memory. At step 1108, a moving average is applied to the R-R interval to minimize localized distortions in the stored R-R sense interval. In one embodiment, a four-point moving average is applied to the R-R interval, although in other embodiments other types of moving averages may be employed. At step 1110, blanking periods including the T-wave blanking period and P-wave blanking period are removed from the averaged EGM signal. The purpose of extracting the blanking periods from the averaged EGM signal is to prevent the sensing of T-waves and P-waves in subsequent steps. If it is desirable to sense T-waves and/or P-waves, the blanking periods may be modified accordingly.

At step 1112, the secondary threshold is calculated and/or selected. In one embodiment the secondary threshold is selected as a function of the magnitude of the previously sensed R-wave. However, because the secondary threshold does not decay once selected, the secondary threshold is selected to equal a value that will lead to detection of events such as PVC beats. In one embodiment, the secondary threshold is a fixed value (e.g., 50 µV). In other embodiments, the secondary threshold may be selected as a function of the r-wave amplitude (e.g., 12% of "large" r-wave amplitudes and 40% of "smaller" r-wave amplitudes). In addition, if the magnitude of the previously sensed R-wave is below a threshold value (e.g., 100 µV), then rather than set the secondary threshold to a value that may result in the over-sensing of artifacts/noise events, the secondary threshold is set to a nominal value (e.g., 50 µV).

At step 1114, the averaged EGM signal is compared to the secondary threshold to detect additional events within the R-R interval that resulted in the bradycardia detection. An event is detected when the averaged EGM signal exceeds the value of the secondary threshold. At step 1116, the secondary R-R intervals detected as a result of additionally sensed events within the initial R-R interval is compared to the bradycardia interval. It is possible that despite the detection of additional events in the initial R-R interval, the resulting secondary R-R intervals still exceed the bradycardia interval, and thus the bradycardia sense event is still confirmed.

If the secondary sense interval is greater than the bradycardia threshold, then the bradycardia sense event is confirmed at step 1118. If the secondary R-R sense interval is less than the bradycardia interval, the detected bradycardia event is rejected at step 1120. In other embodiments, other rules may be utilized to confirm or deny the bradycardia sense event (e.g., any sense event in the secondary channel will lead to a rejection of a bradycardia sense event irrespective intervals). For example, an additional rule may require that the resulting secondary R-R intervals must also be greater than a threshold value (e.g., 200 ms) to prevent P-wave over-sensing. In this way, the embodiment shown in FIG. 11 provides a method of detecting and verifying bradycardia events that only requires modifications to the installed firmware within a monitoring device or system.

The system and methods described above for reducing inappropriate detection of bradycardia sense events may be extended to reducing inappropriate pause detection, which refers to an asystole event defined as no ventricular events over a defined period of time (e.g., four seconds).

Inappropriate Asystole Detection

Figure 12A:
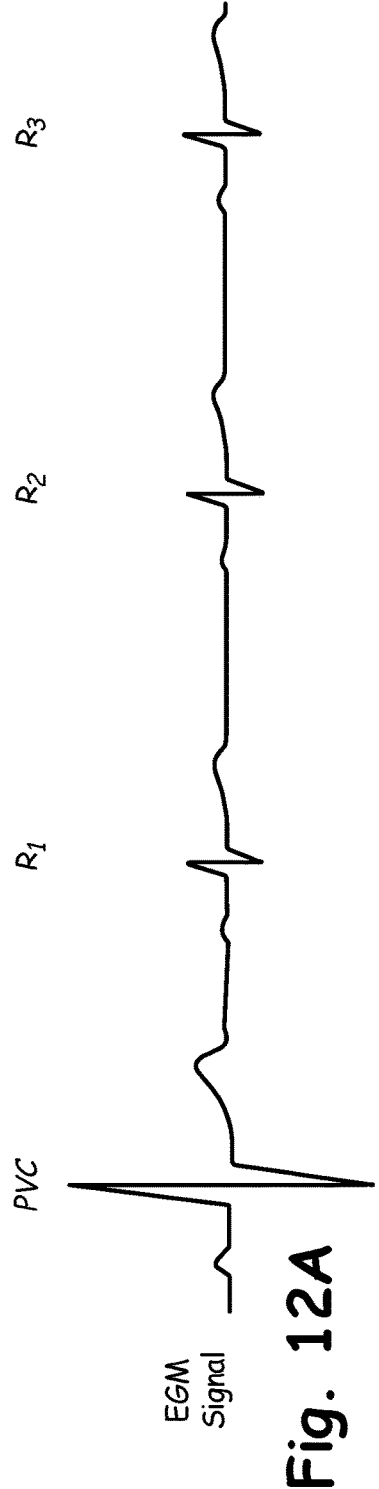
FIG. 12A illustrates an example EGM signal.
Figure 12B:
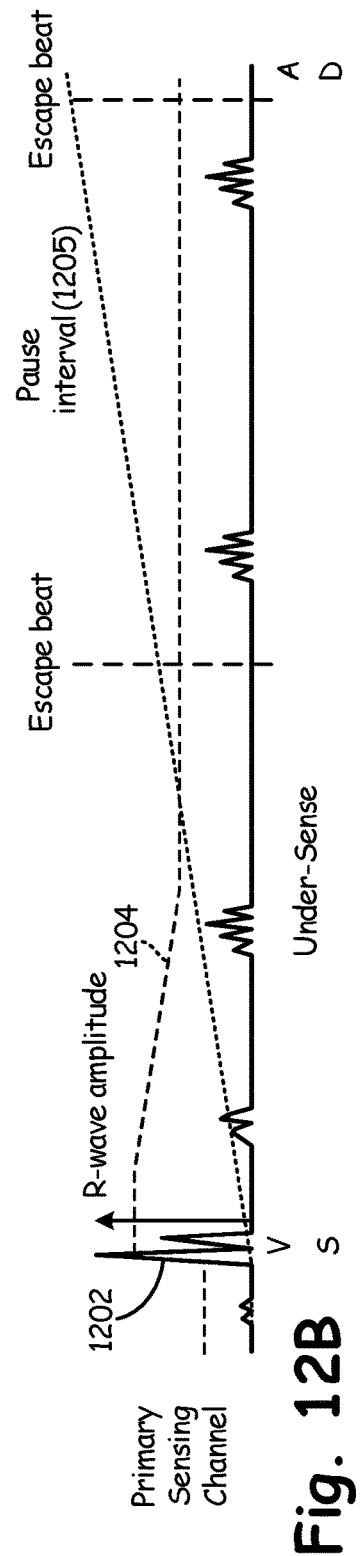
FIG. 12B illustrates processing of the EGM signal within a first channel and resulting under-sensing of ventricular events that results in an inappropriate pause/asystole detection.
Figure 12C:
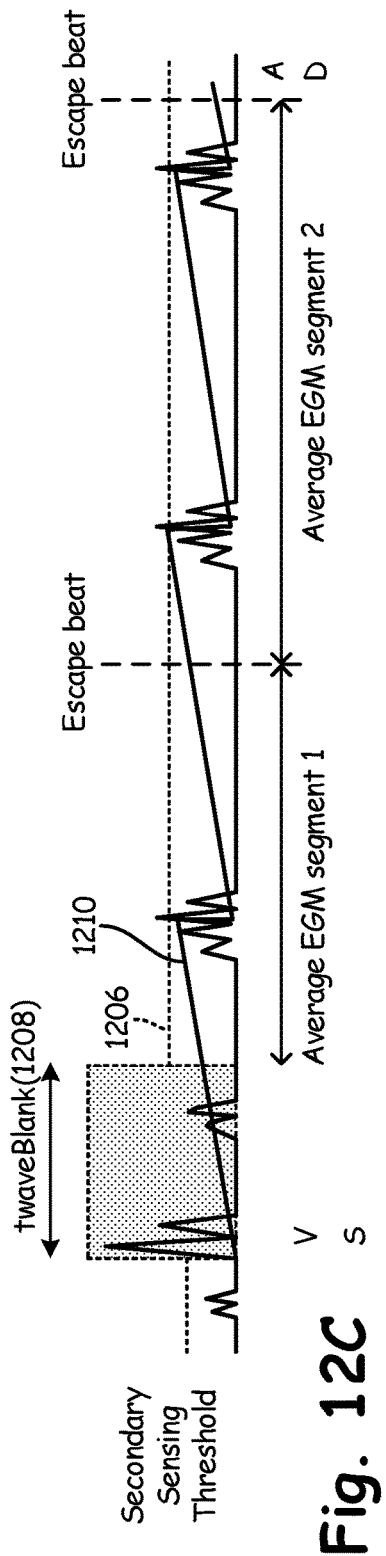
FIG. 12C illustrates processing of the EGM signal using a secondary threshold and secondary timer to detect the under-sensed ventricular events and reject the detected pause/asystole detection according to an embodiment of the present invention.

FIGS. 12A-12C illustrate graphically the use of a secondary threshold and secondary timer to confirm or reject a pause or asystole event detected in the primary sensing channel. In particular, FIG. 12A illustrates a raw electrogram (EGM) signal having a PVC beat followed by three consecutive R-waves R1, R2, and R3. FIG. 12B the EGM signal following filtering/rectification, and further shows the under-sensing of the R-waves R1, R2, and R3 by the primary sensing channel, which leads to an improper pause detection. FIG. 12C illustrates the use of a secondary sensing threshold to detect the under-sensed R-waves R1, R2, and R3 and reject the inappropriate pause detection. One difference between the reduction of inappropriate bradycardia sense events described with respect to FIGS. 5-11 and the reduction of inappropriate pause/asystole detections shown in FIGS. 12A-12C and 13 is that the bradycardia sense events were detected with respect to R-R intervals, whereas pause detections can be based on a detected escape beat or a detected sense event. The escape beat may be followed by a subsequent sense event (e.g., R-wave) or may include a sense event followed by an escape beat.

For example, with respect to FIG. 12B, the PVC beat is detected and the primary sense threshold 1204 (in this embodiment, an auto-adjust threshold) is reset and begins to decay to a minimum or floor value. However, due to the magnitude of the PVC beat, the primary sense threshold decays to a value that is still greater than the amplitude of the successive filtered/rectified R-waves R1, R2, and R3. As a result, each of the successive R-waves R1, R2, and R3 is under-sensed by the primary sensing channel. Following expiration of an escape beat (e.g., occurring either 2 seconds or 4 seconds after the previous R-wave sense) without another sensed event, a cardiac pause or asystole is detected. For example, in the embodiment shown in FIG. 12B, the pause interval 1205 has not been reset by a detected sense, and therefore has increased to a magnitude indicating a cardiac pause or asystole.

In response to the detected pause or asystole, a secondary threshold 1206 is utilized to detect under-sensed events within the pause interval. In the embodiment shown in FIG. 12C, the secondary threshold 1206 is a function of the magnitude of the previously sensed event (in this case the PVC beat), and includes a T-wave blanking period 1208. The embodiment shown in FIG. 12C utilizes a secondary threshold 1206 that may be implemented in firmware, similar to that shown in FIGS. 10A-10C and 11. However, in other embodiments a secondary sense channel may be utilized to detect the under-sensed events, similar to that shown in FIGS. 5-9. For example, rather than a secondary threshold, a second sensing channel may be employed that utilizes a secondary auto-adjust threshold.

In response to the sense event that begins the detected pause interval, a secondary timer 1210 begins to run and continues until the next event is sensed utilizing the secondary threshold 1206. For example, in the embodiment shown in FIG. 12C, R-wave R1 is sensed, resulting in secondary timer 1210 being reset to zero. If no events are sensed, then secondary timer 1210 continues to increment until the escape beat is reached, at which time the secondary timer 1210 is compared to the pause interval threshold or asystole detection interval. If the secondary timer 1210 is greater than the pause interval threshold, then the pause or asystole event detected by the primary channel is verified. If the secondary timer 1210, on account of being reset as a result of a sensed event, is less than the pause interval, then the pause interval (or asystole) detected by the primary sense channel is determined to have been erroneous and is discarded.

Figure 13:
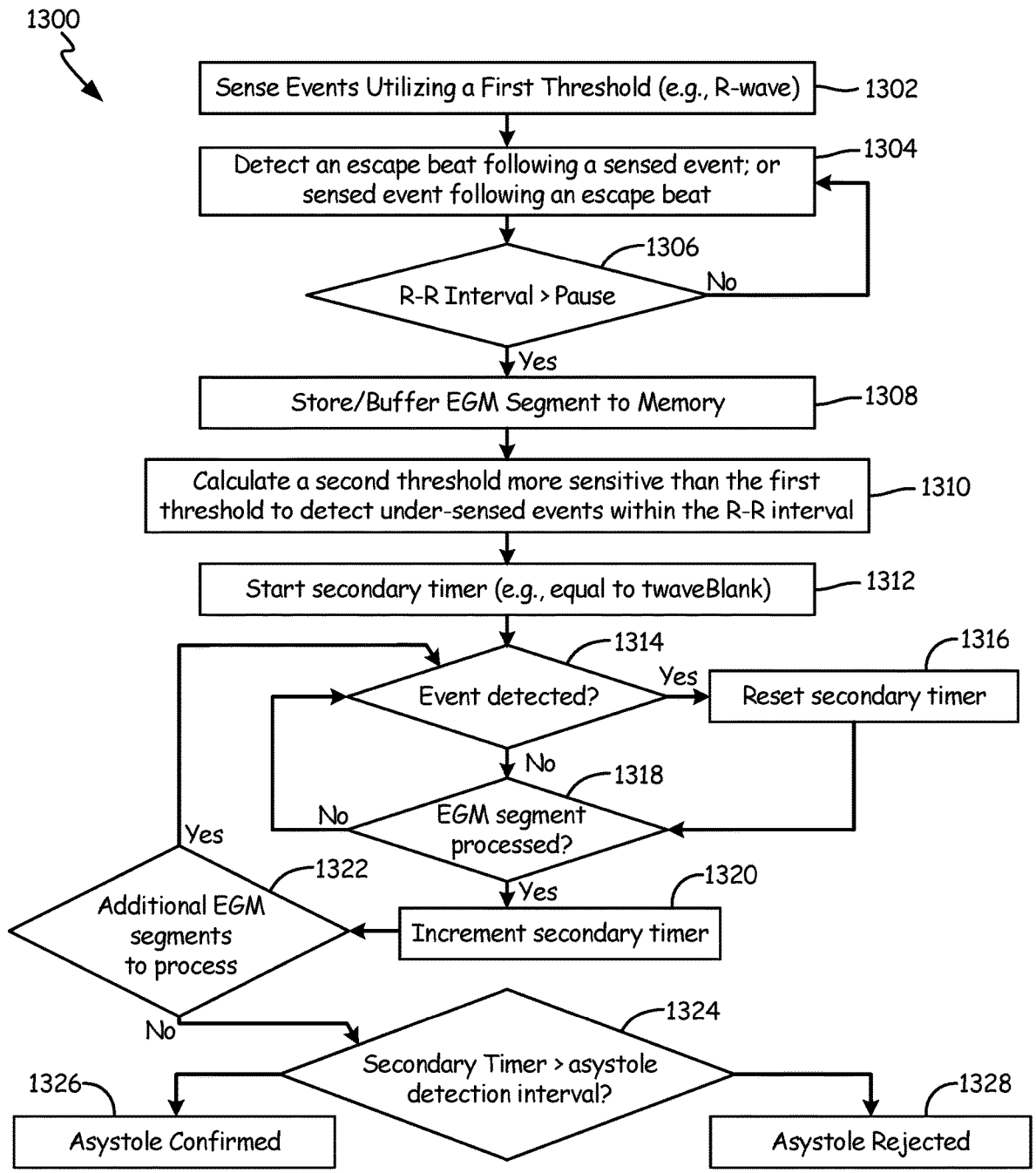
FIG. 13 is a flowchart of a method of detecting and validating pause/asystole intervals utilizing a secondary threshold and secondary timer according to an embodiment of the present invention.

FIG. 13 is a flowchart of a method of detecting and validating pause intervals utilizing a secondary threshold and secondary timer according to an embodiment of the present invention. At step 1302 events are sensed in the primary sense channel using a first threshold. Sensed events may include r-waves, PVC beats, etc. At step 1304 either an escape beat is detected following a sensed event or an event is sensed following an escape beat. In either case, the detection of an escape beat triggers a comparison of the interval between the sensed event and the escape beat (labeled here as the R-E interval) to a pause interval at step 1306. If at step 1306 the R-E interval is determined to be less than the pause interval, then no pause or asystole event is detected and the process continues at step 1302. However, if at step 1306 the R-E interval is determined to be greater than the pause interval, then a pause or asystole event is detected and the process continues at steps 1108-1128 to verify the detected pause or asystole event.

In the embodiment shown in FIG. 13, at step 1308 the EGM segment that resulted in the pause or asystole detect is stored/buffered to memory and processed. The embodiment shown in FIG. 13 relies on a firmware implementation wherein the EGM segment(s) that resulted in the detected pause interval is buffered/stored and analyzed using a calculated secondary threshold. In other embodiments, the EGM segment may be provided to a secondary channel that includes a secondary auto-adjust threshold utilized to detect events in the pause interval. In this latter embodiment, it may not be necessary to store/buffer the EGM segment to memory for processing as the processing may be done contemporaneously with processing of the first channel. Processing the EGM segment includes applying a moving average filter of single sample difference to the raw EGM segment that represents the pause or asystole event to obtain an averaged EGM segment. In one embodiment, this includes applying a four-point moving average filter of the single sample difference to the raw EGM signal that represents the pause or asystole segment (this includes applying the moving average from a previous sense (e.g., $VSENSE_{n-1}$) or escape beat (e.g., $ESCAPE_{n-1}$) to a current escape beat (e.g., $ESCAPE_n$) or current sense (e.g., $VSENSE_n$). In addition, processing of the EGM segment may include extracting portions of the averaged/filtered EGM segment to account for blanking periods utilized to avoid over-sensing P-waves and T-waves. For example, if the ECG segment is measured from a previous sense ($VSENSE_{n-1}$) to a current escape beat ($ESCAPE_n$), then the average EGM segment extracted accounts for a blanking period (twaveBlank) that immediately follows the previous sense ($VSENSE_{n-1}$). This is illustrated graphically in FIG. 12C, which illustrates a t-wave blanking period 1208 extending from the previous sensed event (in this case, a PVC beat). In this way, the portion of the EGM segment analyzed extends from the previously sensed event ($VSENSE_{n-1}$+twaveBlank) to the current escape beat ($ESCAPE_n$). If the EGM segment extends from a previous escape beat ($ESCAPE_{n-1}$) to a current escape beat ($ESCAPE_n$), then no blanking periods are utilized and the extracted filtered/averaged EGM segment extends from the previous escape beat ($ESCAPE_{n-1}$) to the current escape beat ($ESCAPE_n$). Finally, if the EGM segment extends from a previous escape beat ($ESCAPE_{n-1}$) to a current sense ($VSENSE_n$), then the extracted filtered/averaged EGM segment extends from the previous escape beat ($ESCAPE_{n-1}$) to the current sense event minus a p-wave blanking period ($VSENSE_n$–pwaveBlank).

At step 1310 a second threshold is calculated that is more sensitive than the first threshold to allow for the detection of events under-sensed by the first threshold. In one embodiment, the magnitude of the second threshold is a function of the magnitude of the previously sensed event (e.g., 30% of the magnitude of the previously sensed event). In addition, if the previously sensed event is less than a nominal value (e.g., 100 μV), then the second threshold may be set equal to a predetermined value (e.g., half of the nominal value or 50 μV).

At step 1312 the secondary timer is started. In one embodiment, the secondary timer is assigned a timer value of twaveBlank in response to a previous sense event ($VSENSE_{n-1}$).

At step 1314, with the secondary timer running, the filtered/averaged EGM segment is compared with the secondary threshold. An event is detected in response to any point in the filtered/averaged EGM signal exceeding the value of the secondary threshold. If a VSENSE event is detected at step 1314, then at step 1316 the secondary timer is reset to zero, and the method continues at step 1318 to determine whether the EGM segment has been processed. Resetting the secondary timer to zero indicates that an event has been sensed that was not previously sensed, and therefore that the pause or asystole event will need to be reevaluated from the location of the previously under-sensed event. An example of this is shown in FIG. 12C, in which detection of R-wave $R_1$ by the secondary threshold results in secondary timer being reset to zero, before beginning to increase or increment. If no event is detected at step 1314, then the secondary timer continues to increment/increase and a determination is made at step 1318 of whether processing of the EGM segment is complete.

If at step 1318 it is determined that the EGM segment has not been processed, then the method continues at step 1314 in processing the EGM segment for previously under-sensed events. If at step 1318 it is determined that the EGM segment has been processed, then at step 1320 the secondary timer is incremented (if not incrementing continuously) and the method continues at step 1322 to determine whether additional EGM segments need to be processed. If it is determined that additional EGM segments do need to be processed then the method continues at step 1314. If it is determined that all EGM segments in the pause interval have been processed, then at step 1324 the duration of the secondary timer is compared to the pause/asystole threshold. If the secondary timer is greater than the pause/asystole threshold—indicating that the secondary timer was not reset or at least was not reset very often as a result of detecting previously under-sensed events—then the pause or asystole event detected via the primary channel is confirmed at step 1326. If, on the other hand, the secondary timer is NOT greater than the pause/asystole threshold then the pause/asystole event detected in the primary channel is rejected.

In this way, the present disclosure provides a system and method of detecting and verifying events characterized by long intervals between sensed events, such as bradycardia events, cardiac pause events, and asystole events. In particular, the system and methods make use of a primary channel for detecting the condition, and then a secondary threshold/channel for verifying the detected condition. The purpose of the secondary threshold/channel is to detect events that were under-sensed in the primary channel. For example, the secondary threshold/channel may be designed to detect premature ventricular contractions (PVCs) that follow a normal QRS complex (r-wave).

Discussion of Possible Embodiments

The following are non-exclusive descriptions of possible embodiments of the present invention.

A method of verifying detected bradycardia and/or asystole. The method may include sensing an electrogram (EGM) signal. In addition, the method may include comparing an amplitude of the EGM signal to a primary threshold to sense events in the EGM signal and detecting at least one of a bradycardia or an asystole based on the sensed events. In response to detecting at least one of a bradycardia or an asystole, the EGM signal may be compared to a secondary threshold to sense events under-sensed by the primary threshold. Based on the detection of under-sensed events, the method may determine whether the bradycardia or the asystole detected is false.

The method of the preceding paragraph can optionally include, additionally and/or alternatively any, one or more of the following features, configurations and/or additional components.

The method may further include wherein the primary threshold is an auto-adjusted threshold and the secondary threshold is an auto-adjusted threshold. In addition, the method may further include wherein the secondary auto-adjusting threshold decays to a minimum value more quickly than the primary auto-adjusting threshold. In addition, the method may further include wherein the secondary auto-adjusting threshold is initialized to a maximum value following a sense event, wherein the maximum value is a function of an amplitude of the sensed event, and wherein the maximum value associated with the secondary auto-adjusting threshold is less than a maximum value associated with the primary auto-adjusting threshold.

The method may further include filtering and rectifying the sensed EGM signal in a primary sense channel and applying the primary auto-adjust threshold to the filtered/rectified EGM signal. In addition, the method may include applying the secondary auto-adjust threshold to the filtered/rectified EGM signal.

The method may further include filtering and rectifying the sensed EGM signal in the secondary sense channel to generate a secondary filtered/rectified EGM signal. The secondary auto-adjust threshold may then be applied to the secondary filtered/rectified EGM signal, wherein filtering in the secondary sense channel may select lower frequency components than filtering in the primary sense channel.

The method may further include starting a secondary timer in response to a detected asystole. In addition, the secondary timer may be reset in response to detection of an under-sensed event via application of the secondary threshold. The detected asystole may be determined to be false based on the value of the secondary timer.

The method may further include starting the secondary timer in response to at least one of a sensed event or escape beat that marks a beginning of the detected asystole.

In another embodiment, a medical device may include a sensing unit, a primary sensing channel, a secondary sensing channel, and a processor. The sensing unit may monitor an EGM signal, and the primary sensing channel may apply a primary threshold to the EGM signal to detect sense events within the EGM signal. In addition, a secondary sensing channel may apply a secondary threshold to the EGM signal to detect under-sensed events within the EGM signal. The a processor may detect at least one of bradycardia or asystole based on sense events detected by the primary sensing channel, wherein the processor determines whether the detected bradycardia or asystole is false based on detection of under-sensed events by the secondary sensing threshold.

The medical device of the preceding paragraph can optionally include, additionally and/or alternatively any, one or more of the following features, configurations and/or additional component.

For example, the primary threshold utilized by the medical device may be a primary auto-adjusting threshold and the secondary threshold may be a secondary auto-adjusting threshold, wherein the secondary auto-adjusting threshold may decay to a minimum value more quickly than the primary auto-adjusting threshold.

The secondary auto-adjusting threshold of the medical device may be initialized to a maximum value following a sense event, wherein the maximum value may be a function of an amplitude of the sensed event, and wherein the maximum value associated with the secondary auto-adjusting threshold may be less than a maximum value associated with the primary auto-adjusting threshold.

The primary sensing channel of the medical device may further include a primary band-pass filter applied to the monitored EGM signal to generate a filtered EGM signal utilized by the primary threshold.

The secondary sensing channel of the medical device may further include a secondary band-pass filter applied to the monitored EGM signal to generate a secondary filtered EGM signal utilized by the secondary threshold to detect under-sensed events.

In another embodiment, a medical device may include a sensing unit, a primary sensing channel, a processor and a memory unit. The sensing unit may monitor an electrogram (EGM) signal. The primary sensing channel may apply a primary threshold to the EGM signal to detect sense events within the EGM signal. The processor may detect at least one of bradycardia or asystole based on sense events detected by the primary sensing channel. The memory unit may store the EGM segments associated with a detected bradycardia or asystole, wherein the processor may determine whether the detected bradycardia or asystole is false by applying a secondary threshold to the stored EGM segments to detect under-sensed events in the EGM segments.

The medical device of the preceding paragraph can optionally include, additionally and/or alternatively any, one or more of the following features, configurations and/or additional components.

The processor of the medical device may calculate an amplitude of the secondary threshold based on an amplitude of a sensed event in the stored EGM segment.

The processor of the medical device may remove blanking periods from the stored EGM segment to prevent the secondary threshold from sensing T-waves and P-waves.

In another embodiment, the medical device may further include means for sensing an electrogram (EGM) signal. The medical device may include means for comparing an amplitude of the EGM signal to a primary threshold to sense events in the EGM signal and may include means for detecting at least one of a bradycardia or an asystole based on the sensed events. The medical device may also include a means for comparing the EGM signal to a secondary threshold to sense events under-sensed by the primary threshold in response to detecting at least one of a bradycardia or an asystole. The medical device may further include means for determining whether the detection of the bradycardia or the asystole is false based on the detection of under-sensed events.

The medical device of the preceding paragraph can optionally include, additionally and/or alternatively any, one or more of the following features, configurations and/or additional components.

The medical device may detect a bradycardia if an interval between sense events in the EGM signal is greater than a bradycardia threshold, wherein the bradycardia event may be verified if the secondary threshold does not detect under-sensed events in the interval between sense events.

The medical device may further include a secondary timer that is initialized and started in response to a detected asystole, wherein the secondary timer may be reset in response to detection of an under-sensed event by the secondary threshold, and wherein the detected asystole is determined to be false based on the value of the secondary timer following the asystole.

In another embodiment, an insertable cardiac monitor includes a first electrode located at a distal end of the insertable cardiac monitor and a second electrode located at a proximal end of the insertable cardiac monitor. The insertable cardiac monitor may further include a sensing unit coupled to the first and second electrode to monitor an electrogram (EGM) signal and a primary sensing channel that applies a primary threshold to the EGM signal to detect sense events within the EGM signal. A processor may be utilized to detect at least one of bradycardia or asystole based on sense events detected by the primary sensing channel. In addition, the insertable cardiac monitor may include a secondary sensing channel that applies a secondary threshold to the EGM signal to detect under-sensed events within the EGM signal. The processor may further be utilized to determine whether the detected bradycardia or asystole is false based on detection of under-sensed events by the secondary sensing threshold.

The medical device of the preceding paragraph can optionally include, additionally and/or alternatively any, one or more of the following features, configurations and/or additional components.

The insertable cardiac monitor may further include a housing having a length, a width and a depth, wherein the length is much greater than the width and the width is greater than the depth.

The primary threshold utilized by the primary sensing channel may be a primary auto-adjusting threshold. In addition, the secondary threshold utilized by the secondary sensing channel may be a secondary auto-adjusting threshold, wherein the secondary auto-adjusting threshold decays to a minimum value more quickly than the primary auto-adjusting threshold.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

What is claimed is:

1. An insertable cardiac monitor comprising:
   a housing configured for subcutaneous implantation within a patient, the housing having a length, a width, and a depth,
   wherein the length is greater than the width and the width is greater than the depth,
   wherein the length is within a range from 40 millimeters (mm) to 60 mm,
   wherein the width is within a range from 3 mm to 10 mm, and
   wherein the depth is within a range from 2 mm to 5 mm;
   a distal electrode;
   a proximal electrode; and
   circuitry comprising a processer within the housing, the circuitry configured to:
      sense a cardiac signal of the patient via the distal electrode and the proximal electrode;
      compare an amplitude of the cardiac signal to a threshold;
      detect an R-wave based on the comparison of the amplitude of the cardiac signal to the threshold;
      detect an asystole based on a comparison of the amplitude of the cardiac signal subsequent to the detected R-wave to the threshold; and
      further process the cardiac signal sensed during a pause interval that is subsequent to the detected R-wave to determine whether the asystole is false in response to detecting the asystole.

2. The insertable cardiac monitor of claim 1, wherein the threshold comprises a primary threshold, and wherein, to further process the cardiac signal sensed during the pause interval to determine whether the asystole is false, the circuitry is configured to compare a value that is based on the cardiac signal sensed during the pause interval to a secondary threshold.

3. The insertable cardiac monitor of claim 2, wherein, to further process the cardiac signal sensed during the pause interval to determine whether the asystole is false, the circuitry is configured to determine whether an amplitude of the cardiac signal sensed during the pause interval exceeds the secondary threshold.

4. The insertable cardiac monitor of claim 2, wherein the circuitry is configured to determine the secondary threshold based on the detected R-wave.

5. The insertable cardiac monitor of claim 4, wherein, to determine the secondary threshold based on the detected R-wave, the circuitry is configured to:
   determine an amplitude of the detected R-wave; and
   determine the secondary threshold based on the amplitude of the detected R-wave.

6. The insertable cardiac monitor of claim 1, wherein the length is within a range from 40 millimeters (mm) to 45 mm.

7. The insertable cardiac monitor of claim 1, wherein a spacing between the distal electrode and the proximal electrode is within a range from 35 millimeters (mm) to 55 mm.

8. The insertable cardiac monitor of claim 7, wherein the spacing between the distal electrode and the proximal electrode is within a range from 35 millimeters (mm) to 40 mm.

9. The insertable cardiac monitor of claim 7, wherein the distal electrode is substantially flat, and the proximal electrode comprises a three-dimensional, curved configuration.

10. The insertable cardiac monitor of claim 9, wherein the housing defines an elongated rectangular prism comprising a rounded distal end and a rounded proximal end.

11. The insertable cardiac monitor of claim 1, wherein a volume of the insertable cardiac monitor is less than 1.5 cubic centimeters.

12. The insertable cardiac monitor of claim 11, wherein a spacing between the distal electrode and the proximal electrode is within a range from 35 millimeters (mm) to 55 mm.

13. The insertable cardiac monitor of claim 1, wherein the housing defines an elongated rectangular prism comprising a rounded distal end and a rounded proximal end.

14. The insertable cardiac monitor of claim 1, wherein, to further process the cardiac signal sensed during the pause interval to determine whether the asystole is false, the circuitry is configured to:
   determine a segment of the cardiac signal sensed during the pause interval; and
   further process the determined segment.

15. The insertable cardiac monitor of claim 1, wherein, to further process the cardiac signal sensed during the pause interval to determine whether the asystole is false, the circuitry is configured to:
   buffer the cardiac signal sensed during the pause interval; and
   further process the buffered cardiac signal subsequent to the pause interval.

16. The insertable cardiac monitor of claim 1, wherein the circuitry is configured to further process the cardiac signal sensed during the pause interval subsequent to the detected R-wave during the pause interval.

17. A system comprising:
   an external programmer; and
   an insertable cardiac monitor comprising:
      a housing configured for subcutaneous implantation within a patient, the housing having a length, a width, and a depth,
      wherein the length is greater than the width and the width is greater than the depth,
      wherein the length is within a range from 40 millimeters (mm) to 60 mm, wherein the width is within a range from 3 mm to 10 mm, and
      wherein the depth is within a range from 2 mm to 5 mm;
      a distal electrode;
      a proximal electrode; and
      circuitry comprising a processer within the housing, the circuitry configured to:
         sense a cardiac signal of the patient via the distal electrode and the proximal electrode;
         compare an amplitude of the cardiac signal to a threshold;
         detect an R-wave based on the comparison of the amplitude of the cardiac signal to the threshold;
         detect an asystole based on a comparison of the amplitude of the cardiac signal subsequent to the detected R-wave to the threshold; and further process the cardiac signal sensed during a pause interval that is subsequent to the detected R-wave to determine whether the asystole is false in response to detecting the asystole.

18. The system of claim 17, wherein the threshold comprises a primary threshold, and wherein, to further process the cardiac signal sensed during the pause interval to determine whether the asystole is false, the circuitry is configured to compare a value that is based on the cardiac signal sensed during the pause interval to a secondary threshold.

19. The system of claim 18, wherein the circuitry is configured to determine the secondary threshold based on the detected R-wave.

20. The system of claim 19, wherein, to determine the secondary threshold based on the detected R-wave, the circuitry is configured to:
  determine an amplitude of the detected R-wave; and
  determine the secondary threshold based on the amplitude of the detected R-wave.

21. The system of claim 17, wherein a spacing between the distal electrode and the proximal electrode is within a range from 35 millimeters (mm) to 55 mm.

22. The system of claim 21, wherein the distal electrode is substantially flat, and the proximal electrode comprises a three-dimensional, curved configuration.

23. The system of claim 22, wherein the housing defines an elongated rectangular prism comprising a rounded distal end and a rounded proximal end.

24. The system of claim 17, wherein a volume of the insertable cardiac monitor is less than 1.5 cubic centimeters.

25. The system of claim 24, wherein the housing defines an elongated rectangular prism comprising a rounded distal end and a rounded proximal end.

26. The system of claim 17, wherein the housing defines an elongated rectangular prism comprising a rounded distal end and a rounded proximal end.

27. The system of claim 17, wherein, to further process further process the cardiac signal sensed during the pause interval to determine whether the asystole is false, the circuitry is configured to:
  determine a segment of the cardiac signal sensed during the pause interval; and
  further process the determined segment.

28. The system of claim 17, wherein, to further process the cardiac signal sensed during the pause interval to determine whether the asystole is false, the circuitry is configured to:
  buffer the cardiac signal sensed during the pause interval; and
  further process the buffered cardiac signal subsequent to the pause interval.

29. The system of claim 17, wherein the circuitry is configured to transmit data to the external programmer via Bluetooth® communication based on the determination of whether the detection of the asystole is false.

* * * * *